(12) United States Patent
Merkel et al.

(10) Patent No.: US 12,013,330 B2
(45) Date of Patent: Jun. 18, 2024

(54) RESIN COMPOSITION AND FLOW CELLS INCORPORATING THE SAME

(71) Applicants: ILLUMINA, INC., San Diego, CA (US); ILLUMINA CAMBRIDGE LIMITED, Cambridge (GB)

(72) Inventors: Timothy J. Merkel, San Diego, CA (US); Wayne N. George, London (GB); Andrew A. Brown, Cambridge (GB); Audrey Zak, San Diego, CA (US); Gianluca Andrea Artioli, Cambridge (GB); Julia Morrison, Grays (GB); Nikolai Romanov, Cambridge (GB); Lorenzo Berti, San Diego, CA (US); Graham Boud, San Diego, CA (US)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 785 days.

(21) Appl. No.: 16/515,849

(22) Filed: Jul. 18, 2019

(65) Prior Publication Data
US 2020/0025670 A1    Jan. 23, 2020

Related U.S. Application Data

(60) Provisional application No. 62/701,246, filed on Jul. 20, 2018.

(51) Int. Cl.
*G03F 7/00* (2006.01)
*C08L 63/00* (2006.01)
(Continued)

(52) U.S. Cl.
CPC .......... *G01N 15/1436* (2013.01); *C08L 63/00* (2013.01); *C08L 83/12* (2013.01); *G03F 7/0002* (2013.01)

(58) Field of Classification Search
CPC ........ C08L 63/00–10; C09D 163/00–10; C09J 163/00–10
See application file for complete search history.

(56) References Cited

U.S. PATENT DOCUMENTS 5,054,872 A * 10/1991 Fan .......................... G02B 6/13
  430/97
5,162,390 A * 11/1992 Tilley ....................... C09D 4/00
  522/75

(Continued)

FOREIGN PATENT DOCUMENTS

CN    101864144 A    10/2010
EP    1794655        12/2011
(Continued)

OTHER PUBLICATIONS

Scifinder Properties of CAS 75960-60-8 (2021).*
(Continued)

*Primary Examiner* — Kregg T Brooks
(74) *Attorney, Agent, or Firm* — Dierker & Kavanaugh, P.C.

(57) ABSTRACT

An example of a resin composition includes an epoxy resin matrix, a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide, and a photoacid generator. When cured, the resin composition has low or no autofluorescence when exposed to blue excitation wavelengths ranging from about 380 nm to about 480 nm or green excitation wavelengths ranging from about 510 nm to about 560 nm.

9 Claims, 5 Drawing Sheets

(51) Int. Cl.
*C08L 83/12* (2006.01)
*G01N 15/1434* (2024.01)

(56) References Cited

U.S. PATENT DOCUMENTS

| | | | | |
|---|---|---|---|---|
| 5,247,026 | A | * 9/1993 | Erickson | C08C 19/06 525/333.3 |
| 8,033,663 | B2 | * 10/2011 | Valeri | G02B 1/043 522/170 |
| 2003/0225199 | A1 | * 12/2003 | Breunig | G03F 7/0755 524/588 |
| 2004/0163570 | A1 | * 8/2004 | Vanmaele | C09D 11/101 106/31.13 |
| 2004/0229165 | A1 | * 11/2004 | Munnelly | B41C 1/1008 430/281.1 |
| 2005/0260522 | A1 | 11/2005 | Weber et al. | |
| 2007/0224084 | A1 | * 9/2007 | Holmes | A61B 5/150022 422/50 |
| 2007/0267134 | A1 | * 11/2007 | Konarski | C08G 59/24 522/170 |
| 2008/0233279 | A1 | * 9/2008 | Smith | B32B 17/10247 428/29 |
| 2010/0125123 | A1 | * 5/2010 | Lichtenhan | C23C 18/1233 525/453 |
| 2010/0141211 | A1 | 6/2010 | Yazami | |
| 2016/0136873 | A1 | 5/2016 | Chouiki | |
| 2016/0310944 | A1 | 10/2016 | Nishimura et al. | |
| 2017/0009071 | A1 | * 1/2017 | Hoshino | C08G 59/4085 |
| 2017/0204290 | A1 | 7/2017 | Simoff et al. | |
| 2017/0327998 | A1 | * 11/2017 | El Hedok | D06M 15/263 |
| 2017/0363545 | A1 | 12/2017 | Halverson et al. | |
| 2018/0179575 | A1 | 6/2018 | George et al. | |

FOREIGN PATENT DOCUMENTS

| | | | |
|---|---|---|---|
| EP | 2717097 | 4/2014 | |
| EP | 3085661 | 12/2017 | |
| JP | 2000044857 A | * 2/2000 | C09D 11/34 |
| JP | 2002520449 A | 7/2002 | |
| JP | 2005075907 A | * 3/2005 | |
| JP | 2007522531 A | 8/2007 | |
| JP | 2017119340 A | 7/2017 | |
| TW | 201038697 A | 11/2010 | |
| TW | 201638670 A | 11/2016 | |
| WO | 0003300 A1 | 1/2000 | |
| WO | 2005079330 A2 | 9/2005 | |
| WO | WO-2016018918 A1 | * 2/2016 | B05D 3/067 |

OTHER PUBLICATIONS

Partial machine translation of JP-2005075907-A (2005).*
Partial machine translation of JP-2000044857-A.*
Decrop, D , et al., "Single-Step Imprinting of Femtoliter Microwell Arrays Allows Digital Bioassays with Attomolar Limit of Detection", ACS Applied Materials & Interfaces, Mar. 7, 2017, 10418-10426.
Kehagias , et al., "Stamp replication for thermal and UV nanoprint lithography using a UV-sensitive silsesquioxane resist", Microelectronic Engineering 86, 2009, 776-778.
Pai, et al., "A Photoresist with Low Fluorescence for Bioanalytical Applications", Anal Chem. Nov. 15, 2007; 79(22); 8774-8780.

* cited by examiner

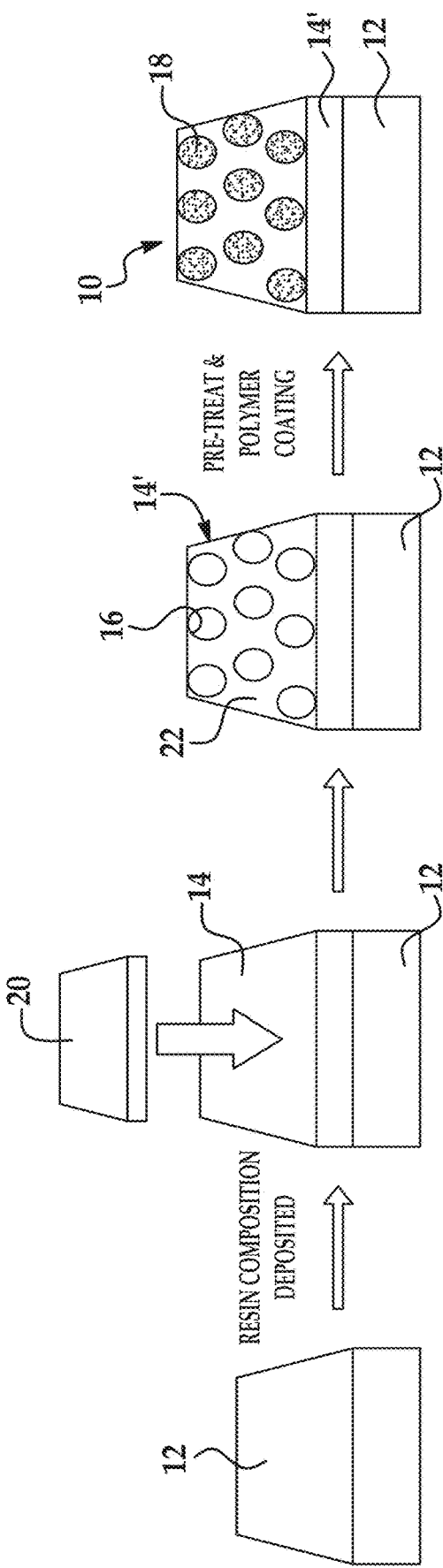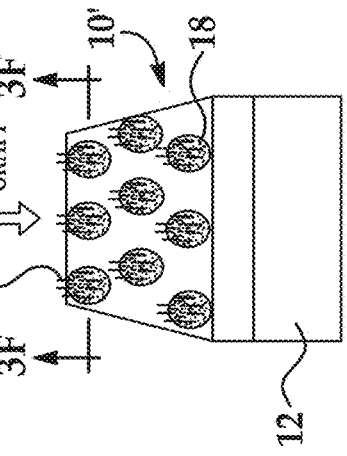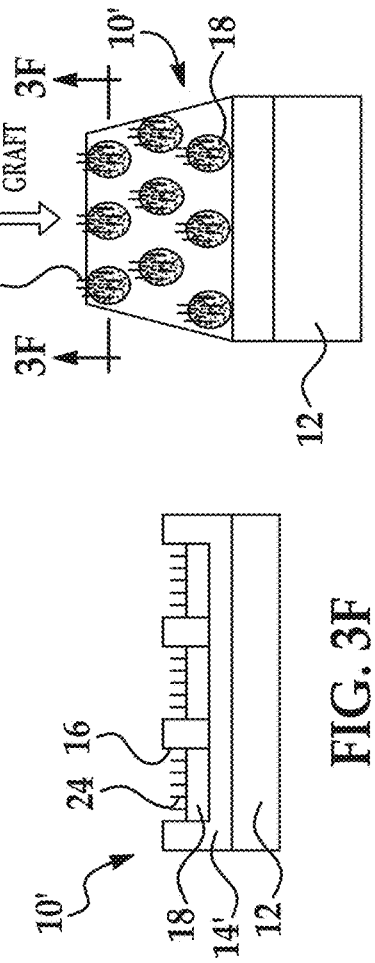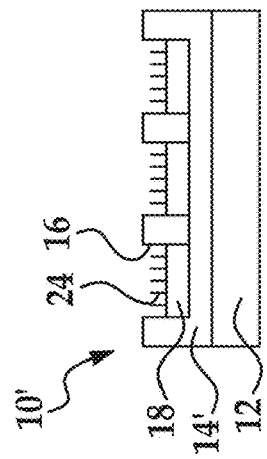

RESIN COMPOSITION AND FLOW CELLS INCORPORATING THE SAME

CROSS-REFERENCE TO RELATED APPLICATIONS

This application claims the benefit of U.S. Provisional Application Ser. No. 62/701,246, filed Jul. 20, 2018, the content of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes in humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

INTRODUCTION

In an aspect, a resin composition comprises an epoxy resin matrix, a free radical photoinitiator selected from the group consisting of: 2-ethyl-9,10-dimethoxyanthracene; 2,2-dimethoxy-2-phenylacetophenone; 2-ethoxy-2-phenylacetophenone; and a phosphine oxide, and a photoacid generator. When cured, the resin composition has low or no autofluorescence when exposed to blue excitation wavelengths ranging from about 380 nm to about 480 nm or green excitation wavelengths ranging from about 510 nm to about 560 nm.

In an example, the cured resin composition has low autofluorescence, wherein the low autofluorescence corresponds with a grey value of less than 25,000 when the cured resin composition is exposed to the blue excitation wavelengths.

In a further example, the cured resin composition has low autofluorescence, wherein the low autofluorescence corresponds with a grey value of less than 5,000 when the cured resin composition is exposed to the blue excitation wavelengths.

In yet a further example, the cured resin composition has low autofluorescence, wherein the low autofluorescence corresponds with a grey value of less than 10,000 when the cured resin composition is exposed to the green excitation wavelengths.

In still another example, the cured resin composition has low autofluorescence, wherein the low autofluorescence corresponds with a grey value of less than 2,500 when the cured resin composition is exposed to the green excitation wavelengths.

Yet in another example, the epoxy resin matrix comprises an epoxy material selected from the group consisting of an epoxy functionalized polyhedral oligomeric silsesquioxane; trimethylolpropane triglycidyl ether; tetrakis(epoxycyclohexyl ethyl)tetramethyl cyclotetrasiloxane; a copolymer of (epoxycyclohexylethyl)methylsiloxane and dimethylsiloxane; 1,3-bis[2-(3,4-epoxycyclohexyl) ethyl] tetramethyl disiloxane; 1,3-bis(glycidoxypropyl)tetramethyl disiloxane; and combinations thereof.

In an example, the epoxy resin matrix includes a combination of two epoxy functionalized polyhedral oligomeric silsesquioxanes, wherein the combination of the two epoxy functionalized polyhedral oligomeric silsesquioxanes includes glycidyl functionalized polyhedral oligomeric silsesquioxane and epoxycyclohexyl ethyl functionalized polyhedral oligomeric silsesquioxane.

In a further example, the free radical photoinitiator is the phosphine oxide, wherein the phosphine oxide is selected from the group consisting of diphenyl(2,4,6-trimethylbenzoyl)phosphine oxide; a blend of diphenyl(2,4,6-trimethylbenzoyl)phosphine oxide and 2-hydroxy-2-methylpropiophenone; phenylbis(2,4,6-,trimethylbenzoyl)phosphine oxide; ethyl(2,4,6-trimethylbenzoyl)phenylphosphinate; and combinations thereof.

In another example, the photoacid generator is selected from the group consisting of N-hydroxynaphthalimide triflate; triarylsulfonium hexafluorophosphate salts, mixed; triarylsulfonium hexafluoroantimonate salts, mixed; 1-naphthyl diphenylsulfonium triflate; 4-phenylthiophenyl)diphenylsulfonium triflate; bis-(4-methylphenyl)iodonium hexafluorophosphate; bis(4-tert-butylphenyl)iodonium hexafluorophosphate; (2-methylphenyl)(2,4,6-trimethylphenyl)iodonium triflate; bis(2,4,6-trimethylphenyl)iodonium triflate; bis-(4-dedecylphenyl)iodonium hexafluoroantimonate salt; and combinations thereof.

In yet another example, the resin composition further comprises a dark quencher or an electron acceptor.

In an example, the free radical photoinitiator and the photoacid generator together are present in an amount ranging from about 1 wt % to about 10 wt %.

In another example, the resin composition further comprises a polyacrylate and propylene glycol monomethylether acetate.

Yet in another example, the epoxy resin matrix further includes a free radical curable resin component including an acrylate and a siloxane.

It is to be understood that any features of this aspect of the resin composition may be combined together in any desirable manner and/or configuration to achieve the benefits as described in this disclosure, including for example the relatively low autofluorescence.

In another aspect, a resin composition comprises an epoxy resin matrix including at least two different epoxy functionalized polyhedral oligomeric silsesquioxanes, and a direct photoacid generator, wherein, when cured, the resin composition has low or no autofluorescence when exposed to blue excitation wavelengths ranging from about 380 nm to about 480 nm or green excitation wavelengths ranging from about 510 nm to about 560 nm.

In an example, the direct photoacid generator is selected from the group consisting of diaryliodonium hexafluorophosphate, diaryliodonium hexafluoroantimonate, and (cumene)cyclopentadienyliron (II) hexafluorophosphate.

In a further example, the at least two different epoxy functionalized polyhedral oligomeric silsesquioxanes include glycidyl functionalized polyhedral oligomeric silsesquioxane and epoxycyclohexyl ethyl functionalized polyhedral oligomeric silsesquioxane.

It is to be understood that any features of this other aspect of the resin composition may be combined together in any desirable manner and/or configuration to achieve the benefits as described in this disclosure, including for example the relatively low autofluorescence.

In another aspect, a flow cell comprises a substrate, and a cured, patterned resin on the substrate, the cured, patterned resin including depressions separated by interstitial regions, and the cured, patterned resin having been formed from a resin composition. The resin composition includes an epoxy resin matrix, a free radical photoinitiator selected from the group consisting of: 2-ethyl-9,10-dimethoxyanthracene; 2,2-dimethoxy-2-phenylacetophenone; 2-ethoxy-2-phenylacetophenone; and a phosphine oxide, and a photoacid generator, wherein the cured, patterned resin has low or no autofluorescence when exposed to blue excitation wavelengths ranging from about 380 nm to about 480 nm or green excitation wavelengths ranging from about 510 nm to about 560 nm.

In an example, the flow cell further comprises a polymer coating in the depressions, and a primer grafted to the polymer coating.

In a further example, the cured, patterned resin has low autofluorescence, wherein the low autofluorescence corresponds with a grey value of less than 5,000 when the cured resin composition is exposed to the blue excitation wavelengths.

In still a further example, the cured, patterned resin has low autofluorescence, and wherein the low autofluorescence corresponds with a grey value of less than 2,500 when the cured resin composition is exposed to the green excitation wavelengths.

In another example, the epoxy resin matrix comprises an epoxy material selected from the group consisting of an epoxy functionalized polyhedral oligomeric silsesquioxane; trimethylolpropane triglycidyl ether; tetrakis(epoxycyclohexyl ethyl)tetramethyl cyclotetrasiloxane; a copolymer of (epoxycyclohexylethyl)methylsiloxane and dimethylsiloxane; 1,3-bis[2-(3,4-epoxycyclohexyl) ethyl] tetramethyl disiloxane; 1,3-bis(glycidoxypropyl)tetramethyl disiloxane; and combinations thereof.

In an example, the epoxy resin matrix includes a combination of two epoxy functionalized polyhedral oligomeric silsesquioxanes, wherein the combination of the two epoxy functionalized polyhedral oligomeric silsesquioxanes includes glycidyl functionalized polyhedral oligomeric silsesquioxane and epoxycyclohexyl ethyl functionalized polyhedral oligomeric silsesquioxane.

In a further example, the free radical photoinitiator is the phosphine oxide, and wherein the phosphine oxide is selected from the group consisting of diphenyl(2,4,6-trimethylbenzoyl)phosphine oxide; a blend of diphenyl(2,4,6-trimethylbenzoyl)phosphine oxide and 2-hydroxy-2-methylpropiophenone; phenylbis(2,4,6-,trimethylbenzoyl) phosphine oxide; ethyl(2,4,6-trimethylbenzoyl) phenylphosphinate; and combinations thereof.

In yet a further example, the photoacid generator is selected from the group consisting of N-hydroxynaphthalimide triflate; triarylsulfonium hexafluorophosphate salts, mixed; triarylsulfonium hexafluoroantimonate salts, mixed; 1-naphthyl diphenylsulfonium triflate; 4-phenylthiophenyl) diphenylsulfonium triflate; bis-(4-methylphenyl)iodonium hexafluorophosphate; bis(4-tert-butylphenyl)iodonium hexafluorophosphate; (2-methylphenyl)(2,4,6-trimethylphenyl)iodonium triflate; bis(2,4,6-trimethylphenyl)iodonium triflate; bis-(4-dedecylphenyl)iodonium hexafluoroantimonate salt; and combinations thereof.

It is to be understood that any features of this aspect of the flow cell may be combined together in any desirable manner to achieve the benefits as described in this disclosure, including for example the relatively low autofluorescence. Moreover, it is to be understood that any combination of features of this aspect of the flow cell and/or either of the resin compositions may be used together, and/or that any features from any of these aspects may be combined with any of the examples disclosed herein to achieve the benefits as described in this disclosure, including for example the relatively low autofluorescence.

In still another aspect, a method of making a flow cell comprises depositing a resin composition on a substrate. The resin composition includes an epoxy resin matrix, a free radical photoinitiator selected from the group consisting of: 2-ethyl-9,10-dimethoxyanthracene; 2,2-dimethoxy-2-phenylacetophenone; 2-ethoxy-2-phenylacetophenone; and a phosphine oxide, and a photoacid generator. The method further comprises nanoimprinting the deposited resin composition using a working stamp, and curing the deposited resin composition to form a cured, patterned resin, wherein the cured, patterned resin has low or no autofluorescence when exposed to blue excitation wavelengths ranging from about 380 nm to about 480 nm or green excitation wavelengths ranging from about 510 nm to about 560 nm.

It is to be understood that any features of this aspect of the method may be combined together in any desirable manner to achieve the benefits as described in this disclosure, including for example the relatively low autofluorescence. Moreover, it is to be understood that any combination of features from the method and/or from the flow cell and/or from the resin compositions may be used together, and/or that any features from any or all of these aspects may be combined with any of the features of the examples disclosed herein to achieve the benefits as described in this disclosure, including for example the relatively low autofluorescence.

Still further, it is to be understood that any features of any of the method and/or of the flow cell and/or of the resin composition may be combined together in any desirable manner, and/or may be combined with any of the examples disclosed herein to achieve the benefits as described in this disclosure, including for example the relatively low autofluorescence.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 3A through 3E are schematic perspective views which together depict examples of the method disclosed herein;

FIG. 3F is a schematic and cross-sectional view taken along line 3F-3F of FIG. 3E;

DETAILED DESCRIPTION

Figure 1:
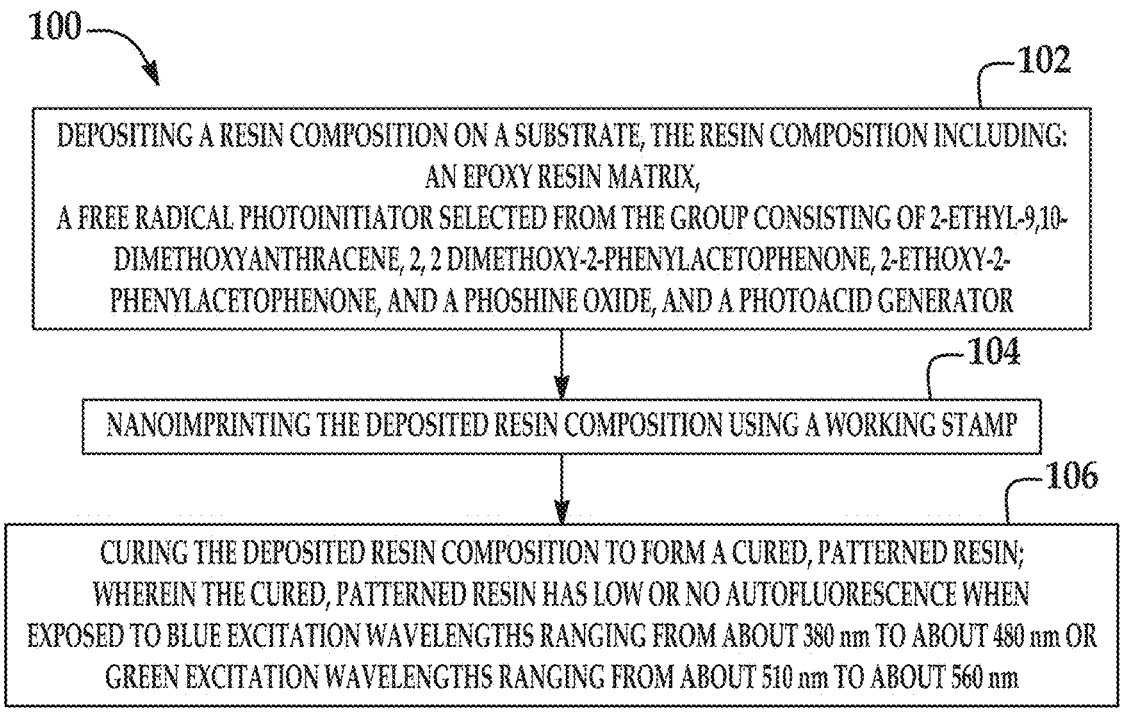
FIG. 1 is a flow diagram illustrating an example of a method disclosed herein.

It is desirable for patterned flow cells used in sequencing applications to have basal levels of autofluorescence that enable signal to noise ratios (SNRs) that are high enough so that signals from individual clusters can be resolved during sequencing. Resin compositions used in patterned flow cells often include photoinitiators (e.g., free radical and/or cationic generators) to initiate curing during patterning of the composition. In theory, when the photoinitiators used have no absorption in the visible region, no fluorescence should occur when excited by the blue, green and/or red light sources used during sequencing. However, it has been found that undesirable autofluorescence may occur at excitation wavelengths of interest (e.g., blue and/or green excitation wavelengths), even when little or no absorbance is predicted to occur based on the spectral properties of the resin components in the visible region. It has also been found (based on solution measurements of some free radical and cationic photoinitiator combinations) that this undesirable autofluorescence may be due to intramolecular interactions between certain combinations of free radical and cationic photoinitiators that occur before or during ultraviolet (UV) light exposure. It is believed that the energy exchange between these particular combinations of free radical and cationic photoinitiators and the subsequent formation of excited state complexes (exciplexes) and adducts may be contributing to the undesirable autofluorescence in blue and/or green excitation wavelengths of interest.

Several epoxy based resin compositions are disclosed herein that, when cured, display autofluorescence in blue and/or green excitation wavelengths of interest that is about an order-of-magnitude lower than those made with the combinations of free radical and cationic photoinitiators mentioned above.

In some examples disclosed herein, the epoxy based resin composition includes a specific photoinitiator package, which includes a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide, and a cationic photoinitiator (a photoacid generator). It is believed that the Norrish Type II anthracene derivative and the Norrish Type I acetophenone or phosphine oxides can generate radicals with UVA exposure, which can contribute to a two-part curing system with the photoacid generator, without undergoing intramolecular interactions that lead to undesirable autofluorescence in blue and/or green excitation wavelengths of interest.

In other examples disclosed herein, the epoxy based resin composition includes a direct photoacid generator. The direct photoacid generator can be used without other types of photoinitiators, such as free radical photoinitiators. This, in turn, can minimize, and in some instances even eliminate, intramolecular interactions that may otherwise occur between some of the different types photoinitiators. Because these other examples of the resin composition disclosed herein do not experience the aforementioned intramolecular interactions, these other examples of the cured resin composition disclosed herein can exhibit no or low autofluorescence (when exposed to blue and/or green excitation wavelengths).

The resin compositions disclosed herein may also be more readily photobleached, which would render the cured resin composition permanently unable to autofluoresce (i.e., any autofluorescence that does occur is below a threshold limit of detection or does not interfere with sequencing detection processes).

As mentioned herein, the examples of the cured resin composition disclosed herein have minimal blue and green emissions, and also exhibit relatively low or no autofluorescence when exposed to blue and green excitation wavelengths. As used herein, blue emission wavelengths include from about 463 nm to about 514, and green emission wavelengths include from about 583 nm to about 660 nm. Also as used herein, blue excitation wavelengths include from about 380 nm to about 480 nm, and green excitation wavelengths include from about 510 nm to about 560 nm. In another example, blue excitation wavelengths include from about 440 nm to about 457 nm, and green excitation wavelengths include from about 519 nm to about 535 nm. In still another example, the blue excitation wavelengths range from about 400 nm to about 480 nm.

In some instances, the cured resin composition is described as having no fluorescence (emission of light) when exposed to blue excitation wavelengths and/or green excitation wavelengths. No fluorescence or no autofluorescence means that the level of fluorescence is below a threshold limit of detection. No fluorescence or no autofluorescence, as the terms are defined herein, may occur when the cured resin composition has been photobleached. In other instances, the cured resin composition fluoresces (emits light) when exposed to blue excitation wavelengths and/or green excitation wavelengths. In these instances, the term "low autofluorescence" may mean that the emission level (of the cured resin when exposed to blue excitation wavelengths and/or green excitation wavelengths) is above the threshold limit of detection, but is low enough to be considered noise, and the noise does not interfere with the identification of cluster signals during sequencing (e.g., the levels of autofluorescence enable signal to noise ratios (SNRs) that are high enough so that signals from individual clusters can be resolved during sequencing).

It is to be understood that the definition of "low" or "low level", in terms of quantifying the autofluorescence, may vary depending upon the tool used to measure the autofluorescence and/or lamps used to provide the excitation radiation. For example, when an Amersham TYPHOON™ (formerly TYPHOON™ FLA 7000) (available from GE Healthcare Life Sciences) is used to measure the autofluorescence of the cured resin compositions upon exposure to blue excitation wavelengths, the low autofluorescence corresponds with a grey value of less than 25,000. For another example, when the Amersham TYPHOON™ is used to measure the autofluorescence of the cured resin compositions upon exposure to blue excitation wavelengths, the low autofluorescence corresponds with a grey value of less than 5,000. For still another example, when the Amersham TYPHOON™ is used to measure the autofluorescence of the cured resin compositions upon exposure to green excitation wavelengths, the low autofluorescence corresponds with a grey value of less than 10,000. For yet a further example, when the Amersham TYPHOON™ is used to measure the autofluorescence of the cured resin compositions upon exposure to green excitation wavelengths, the low autofluorescence corresponds with a grey value of less than 2,500.

Autofluorescence may also be measured using a spectrometer based tool. An example of a spectrometer based tool uses a 445 nm (blue) laser as the excitation source. The laser spot size may be about 200 μm. The laser beam passes through a filter to filter out some higher wavelength lines and then passes through a sample. Transparent samples are used for the measurement. In line with the laser beam on the other side of the sample is a spectrometer (e.g., an Ocean Optics spectrometer) that is fiber-optically coupled. The incident laser power can be tuned by adjusting the drive current or adding attenuating filters in front of the laser beam. In an example, a laser power of 3 mW may be used.

In an example, when a spectrometer based tool is used to measure the autofluorescence of the cured resin compositions upon exposure to blue excitation wavelengths, the low autofluorescence may correspond with a fluorescence intensity (in arbitrary units (AU)) of less than about 400 AU. In another example, when a spectrometer based tool is used to measure the autofluorescence of the cured resin composition upon exposure to green excitation wavelengths, the low autofluorescence may correspond with a fluorescence intensity (in arbitrary units (AU)) of less than about 500 AU.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

An "acrylamide" is a functional group with the structure

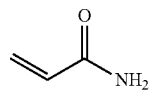

or a monomer including an acrylamide group with that structure. An acrylamide may be the chemical compound acylamide with a substituent in place of one or more hydrogen atoms (e.g., methacrylamide). Examples of the monomer including an acrylamide group include azido acetamido pentyl acrylamide:

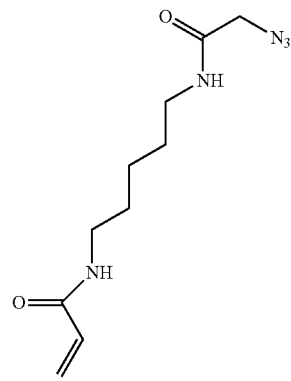 [SMILES: C=CC(=O)NCCCCCNC(=O)CN=[N+]=[N-]]

and N-isopropylacrylamide:

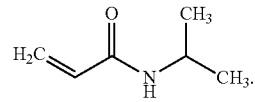

Other acrylamide monomers may be used.

An aldehyde, as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

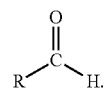

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amino" functional group refers to an —NR$_a$R$_b$ group, where R$_a$ and R$_b$ are each independently selected from hydrogen (e.g., ), C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, the term "attached" refers to the state of two things being joined, fastened, adhered, connected or bound to each other, either directly or indirectly. For example, a nucleic acid can be attached to a polymer coating by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$.

As used herein, a "bonding region" refers to an area on a substrate that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkyl" means any univalent groups derived from cycloalkanes by removal of a hydrogen atom from a ring carbon atom (e.g., from a cycloalkane). An example includes 2-methylcyclopropyl.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "depression" refers to a discrete concave feature in a patterned resin having a surface opening that is at least partially surrounded by interstitial region(s) of the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or a trench/line/trough. The depression may also have more complex architectures, such as ridges, step features, etc.

The term "epoxy" as used herein refers to

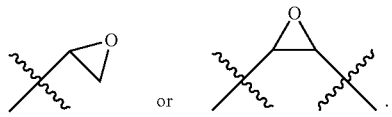

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber/flow channel can include one or more transparent surfaces allowing for the optical detection of arrays, optically labeled molecules, or the like, at the depression.

As used herein, a "flow channel" may be an area defined between two bonded components, which can selectively receive a liquid sample. In some examples, the flow channel may be defined between a patterned resin and a lid, and thus may be in fluid communication with one or more depressions defined in the patterned resin.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

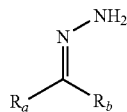

group in which $R_a$ and $R_b$ are each independently selected from hydrogen (e.g., ), C1-C6 alkyl, C2-C6 alkenyl, C2-C6 alkynyl, C3-C7 carbocyclyl, C6-C10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area on a surface (e.g., of a patterned resin) that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the features defined in the surface. For example, features of an array can have an amount or concentration of a polymer coating and primer(s) that exceeds the amount or concentration present at the interstitial regions. In some examples, the polymer coating and primer(s) may not be present at the interstitial regions.

"Nitrile oxide," as used herein, means a "$R_a C \equiv N^+ O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

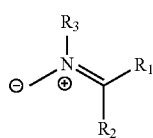

group in which $R_1$, $R_2$, and $R_3$ may be any of the $R_a$ and $R_b$ groups defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

As used herein, a "photoacid generator" (PAG) is a molecule that releases protons upon exposure to radiation. PAGs generally undergo proton photodissociation irreversibly.

As used herein, a "photoinitiator" (PI) is a molecule that undergoes a photoreaction upon absorption of radiation, thereby producing reactive species. Photoinitiators are capable of initiating or catalyzing chemical reactions that result in changes in the solubility and/or physical properties of formulations.

As used herein, the "primer" is defined as a single stranded nucleic acid sequence (e.g., single strand DNA or single strand RNA). Some primers, which may be referred to as amplification primers, serve as a starting point for template amplification and cluster generation. Other primers, which may be referred to as sequencing primers, serve as a starting point for DNA or RNA synthesis. The 5' terminus of the primer may be modified to allow a coupling reaction with a functional group of a polymer coating. The primer length can be any number of bases long and can include a variety of non-natural nucleotides. In an example, the sequencing primer is a short strand, ranging from 10 to 60 bases, or from 20 to 40 bases.

A "spacer layer," as used herein refers to a material that bonds two components together. In some examples, the spacer layer can be a radiation-absorbing material that aids in bonding, or can be put into contact with a radiation-absorbing material that aids in bonding.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

First Example Resin Composition

In some examples disclosed herein, the resin complex includes an epoxy resin matrix, a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide, and a photoacid generator, wherein, when cured, the resin composition has low or no autofluorescence when exposed to blue excitation wavelengths ranging from about 380 nm to about 480 nm or green excitation wavelengths ranging from about 510 nm to about 560 nm. In another example, the blue excitation wavelengths range from about 440 nm to about 457 nm or the green excitation wavelengths range from about 519 nm to about 535 nm.

In this example resin composition, the epoxy resin matrix comprises an epoxy material selected from the group consisting of:

i) an epoxy functionalized polyhedral oligomeric silsesquioxane (POSS) (described further hereinbelow);

ii) trimethylolpropane triglycidyl ether:

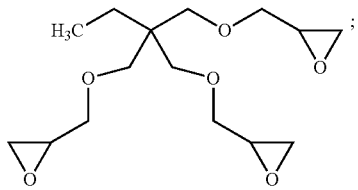 [SMILES: CCC(COCC1CO1)(COCC1CO1)COCC1CO1]

iii) tetrakis(epoxycyclohexyl ethyl)tetramethyl cyclotetrasiloxane:

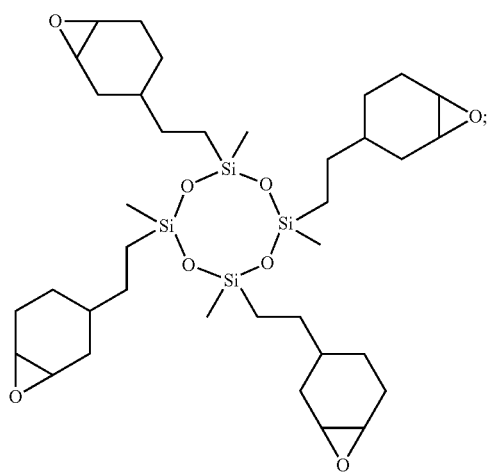 [SMILES: C[Si]1(CCC2CCC3OC3C2)O[Si](C)(CCC2CCC3OC3C2)O[Si](C)(CCC2CCC3OC3C2)O[Si](C)(CCC2CCC3OC3C2)O1]

iv) a copolymer of (epoxycyclohexylethyl)methylsiloxane and dimethylsiloxane:

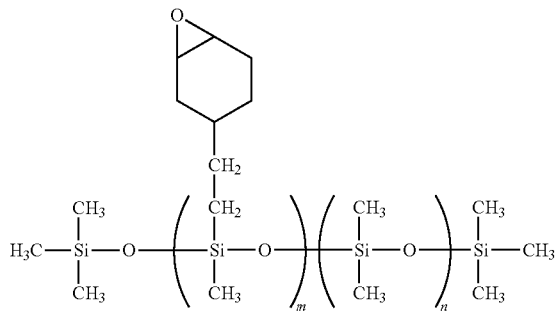

(wherein a ratio of m:n ranges from 8:92 to 10:90);

v) 1,3-bis[2-(3,4-epoxycyclohexyl) ethyl] tetramethyl disiloxane:

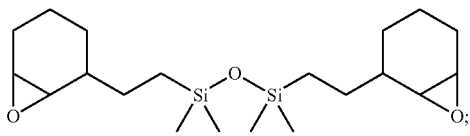 [SMILES: C[Si](C)(CCC1CCCC2OC12)O[Si](C)(C)CCC1CCCC2OC12]

vi) 1,3-bis(glycidoxypropyl)tetramethyl disiloxane:

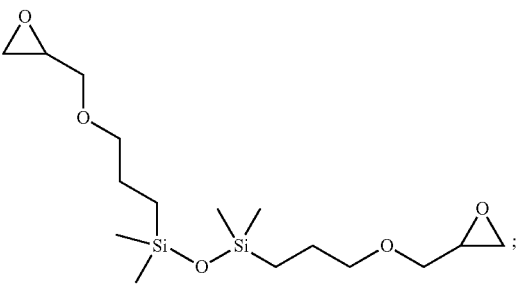 [SMILES: C[Si](C)(CCCOCC1CO1)O[Si](C)(C)CCCOCC1CO1]

and vii) combinations thereof. When combinations are used, it is to be understood that any two or more of the listed epoxy resin matrices may be used together in the resin composition.

The epoxy functionalized polyhedral oligomeric silsesquioxane includes a polyhedral oligomeric silsesquioxane (POSS) core that is functionalized with epoxy groups. As used herein, the term "polyhedral oligomeric silsesquioxane" (POSS) refers to a chemical composition that is a hybrid intermediate ($RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. The composition is an organosilicon compound with the chemical formula $[RSiO_{3/2}]_n$, where the R groups can be the same or different. The resin composition disclosed herein may comprise one or more different cage or core structures as monomeric units. In some instances, the structure includes a polyoctahedral cage or core structure. For example, the polyhedral structure may be a $T_8$ structure, such as:

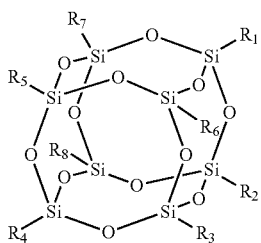

and represented by:

$T_8$.

This monomeric unit typically has eight arms of functional groups $R_1$ through $R_8$.

The monomeric unit may have a cage structure with 10 silicon atoms and 10 R groups, referred to as $T_{10}$, such as:

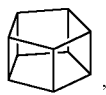

$T_{10}$ or may have a cage structure with 12 silicon atoms and 12 R groups, referred to as $T_{12}$, such as:

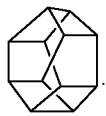

$T_{12}$

The POSS-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein. As examples, any of the cage structures may be present in an amount ranging from about 30% to about 100% of the total POSS monomeric units used. The POSS-based material may be a mixture of cage structures along with open and partially open cage structures. Thus, a POSS-based resin precursor or resin may include epoxy POSS materials, which may be a mixture of silsesquioxane configurations. For example, any POSS material described herein may be a mixture of discrete POSS cages and non-discrete silsesquioxane structures and/or incompletely condensed, discrete structures, such as polymers, ladders, and the like. The partially condensed materials would therefore include epoxy R groups as described herein at some silicon vertices, but some silicon atoms would not be substituted with the R groups and could be substituted instead with OH groups. In some examples, the POSS materials comprise a mixture of various forms, such as:

Condensed cages (a)

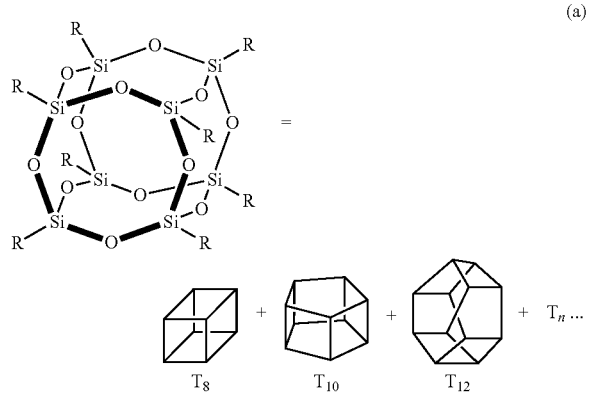

Incompletely Condensed cages (b)

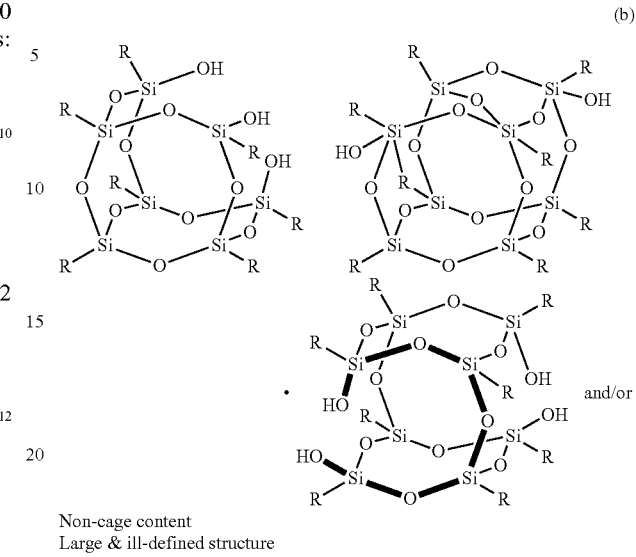

Non-cage content
Large & ill-defined structure (c)

"T-resin"/Polysilsesquioxanes

In the examples disclosed herein, at least one of $R_1$ through $R_8$ or $R_{10}$ or $R_{12}$ comprises an epoxy, and thus the POSS is referred to as an epoxy POSS. In some examples, a majority of the arms, such as the eight, ten, or twelve arms, or R groups, comprise epoxy groups. In other examples, $R_1$ through $R_8$ or $R_{10}$ or $R_{12}$ are the same, and thus each of $R_1$ through $R_8$ or $R_{10}$ or $R_{12}$ comprises an epoxy group. In still other examples, $R_1$ through $R_8$ or $R_{10}$ or $R_{12}$ are not the same, and thus at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group, which in some cases is selected from the group consisting of an azide/azido, a thiol, a poly(ethylene glycol), a norbornene, and a tetrazine, or further, for example, alkyl, aryl, alkoxy, and haloalkyl groups. In some aspects, the non-epoxy functional group is selected to increase the surface energy of the resin. In these other examples, the ratio of epoxy groups to non-epoxy groups ranges from 7:1 to 1:7, or 9:1 to 1:9, or 11:1 to 1:11. In any of the examples, disubstituted or monosubstituted (terminal) epoxy group(s) allow the monomeric unit to polymerize into a cross-linked matrix upon initiation using ultraviolet (UV) light and an acid. In some aspects, the epoxy POSS comprises terminal epoxy groups. An example of this type of POSS is glycidyl POSS having the structure:

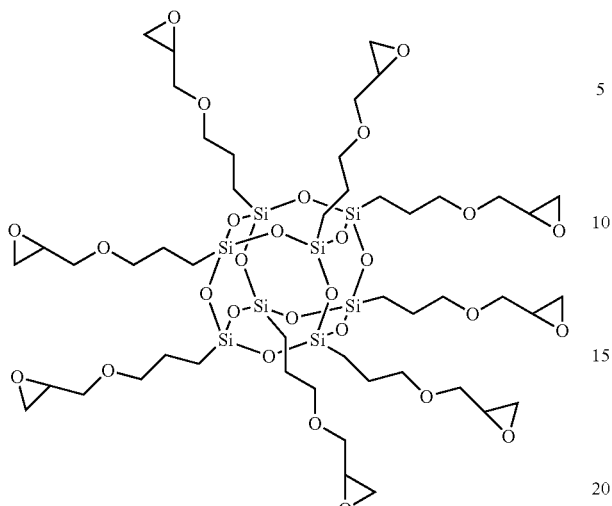

Another example of this type of POSS is epoxycyclohexyl ethyl functionalized POSS having the structure:

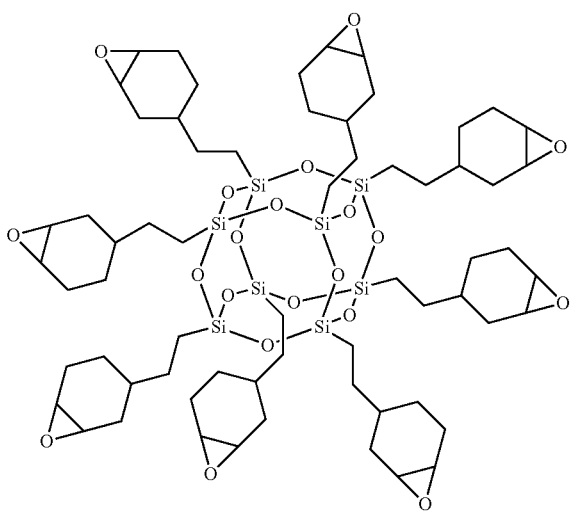 [SMILES: C1CC2OC2CC1CC[Si]12O[Si]3(CCC4CCC5OC5C4)O[Si]4(CCC5CCC6OC6C5)O[Si](CCC5CCC6OC6C5)(O1)O[Si]1(CCC5CCC6OC6C5)O[Si](CCC5CCC6OC6C5)(O2)O[Si](CCC2CCC5OC5C2)(O3)O[Si](CCC2CCC3OC3C2)(O4)O1]

One example of the epoxy resin matrix disclosed herein includes a combination of two epoxy POSS compounds, where the combination includes glycidyl POSS and epoxy-cyclohexyl ethyl functionalized POSS.

In the examples disclosed herein, the epoxy POSS may also be a modified epoxy POSS, that includes a controlled radical polymerization (CRP) agent and/or another functional group of interest incorporated into the resin or core or cage structure as one or more of the functional group $R_1$ through $R_8$ or $R_{10}$ or $R_{12}$.

In these examples of the resin composition, the free radical photoinitiator is selected from the group consisting of 2-ethyl-9,10-dimethoxyanthracene, 2,2-dimethoxy-2-phenylacetophenone, 2-ethoxy-2-phenylacetophenone, and a phosphine oxide.

In some examples, the free radical photoinitiator is 2-ethyl-9,10-dimethoxyanthracene:

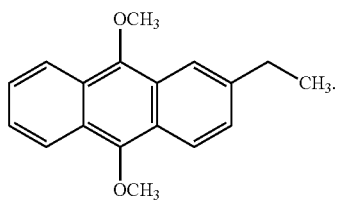 [SMILES: CCc1ccc2c(OC)c3ccccc3c(OC)c2c1]

In other examples, the free radical photoinitiator 2,2-dimethoxy-2-phenylacetophenone:

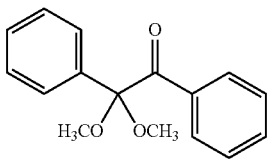 [SMILES: COC(OC)(C(=O)c1ccccc1)c1ccccc1]

In yet other examples, the free radical photoinitiator is 2-ethoxy-2-phenylacetophenone (a.k.a., benzoin ethyl ether):

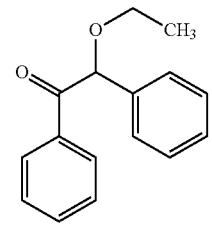

In still other examples, the free radical photoinitiator is the phosphine oxide. When the phosphine oxide is used, it may be selected from the group consisting of:
i) diphenyl(2,4,6-trimethylbenzoyl)phosphine oxide:

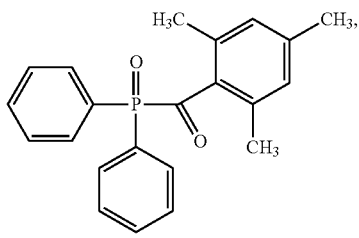 [SMILES: Cc1cc(C)c(C(=O)P(=O)(c2ccccc2)c2ccccc2)c(C)c1]

ii) a blend of diphenyl(2,4,6-trimethylbenzoyl)phosphine oxide and 2-hydroxy-2-methylpropiophenone:

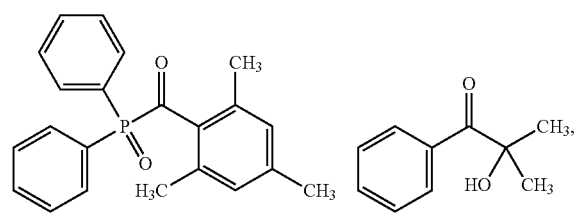

iii) phenylbis(2,4,6-,trimethylbenzoyl)phosphine oxide:

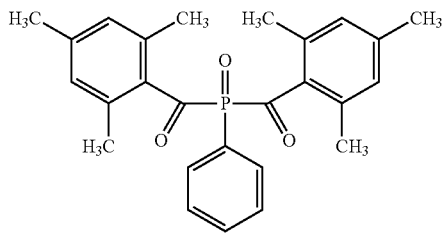

iv) ethyl(2,4,6-trimethylbenzoyl)phenylphosphinate:

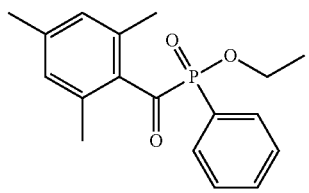 [SMILES: CCOP(=O)(C(=O)c1c(C)cc(C)cc1C)c1ccccc1]

v) combinations thereof. When combinations are used, it is to be understood that any two or more of the listed free radical photoinitiators may be used together in this example of the resin composition.

In addition to the free radical photoinitiator, these examples of the resin composition also include a photoacid generator (PAG). The free radicals generated by the photoinitiator react with the photoacid generator, which decomposes to generate a superacid, which, in turn, initiates the polymerization and/or crosslinking of the epoxy resin matrix component(s). It is believed that any suitable photoacid generator that will not undergo undesirable intramolecular interactions with the free radical photoinitiator may be used. Examples of suitable photoacid generators may include benzyl, imino ester, conjugated imino ester, spiropyran, teraylene-based, two-photon, and organometallic PAG systems.

Some specific examples of suitable photoacid generators are selected from the group consisting of:
i) N-hydroxynaphthalimide triflate:

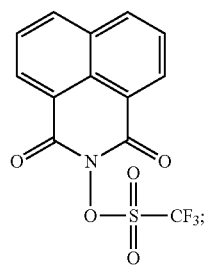 [SMILES: O=C1c2cccc3cccc(c23)C(=O)N1OS(=O)(=O)C(F)(F)F]

ii) triarylsulfonium hexafluorophosphate salts, mixed:

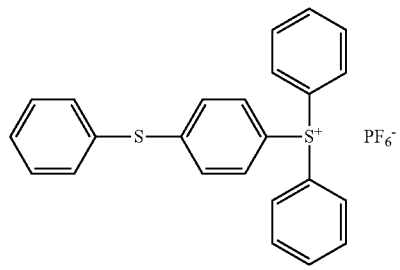

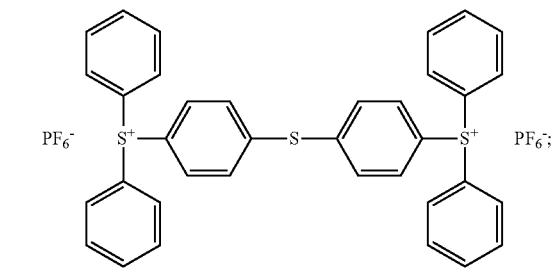

iii) triarylsulfonium hexafluoroantimonate salts, mixed:

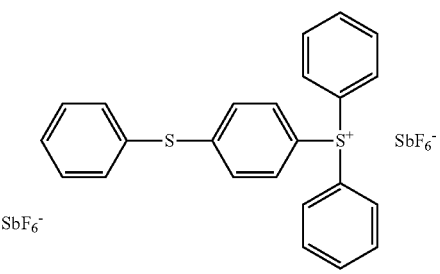

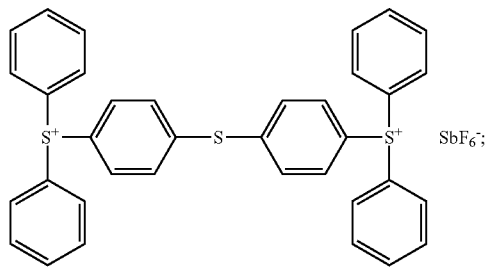

iv) 1-naphthyl diphenylsulfonium triflate (NDS-TF):

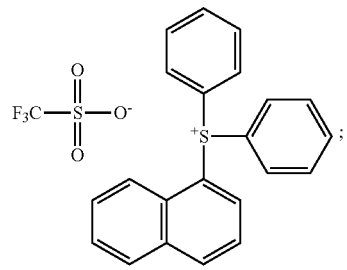 [SMILES: O=S(=O)([O-])C(F)(F)F ; c1ccc([S+](c2ccccc2)c2cccc3ccccc23)cc1]

v) (4-phenylthiophenyl)diphenylsulfonium triflate:

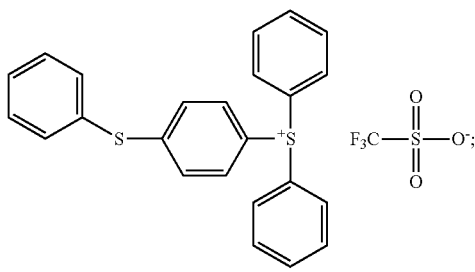

vi) bis-(4-methylphenyl)iodonium hexafluorophosphate:

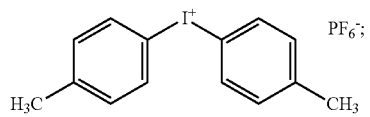

vii) bis(4-tert-butylphenyl)iodonium hexafluorophosphate:

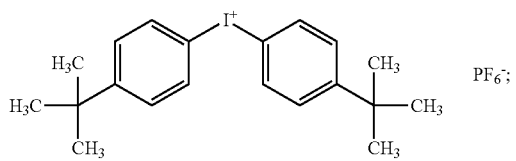 [SMILES: CC(C)(C)c1ccc([I+]c2ccc(C(C)(C)C)cc2)cc1 ; "PF6-;"]

viii) (2-methylphenyl)(2,4,6-trimethylphenyl)iodonium triflate:

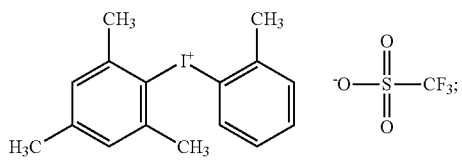

xi) bis(2,4,6-trimethylphenyl)iodonium triflate:

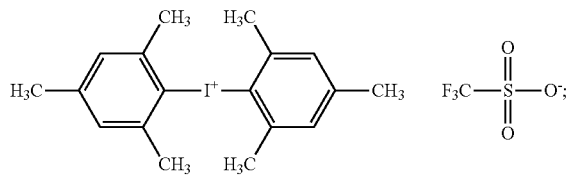

x) bis-(4-dedecylphenyl)iodonium hexafluoroantimonate salt:

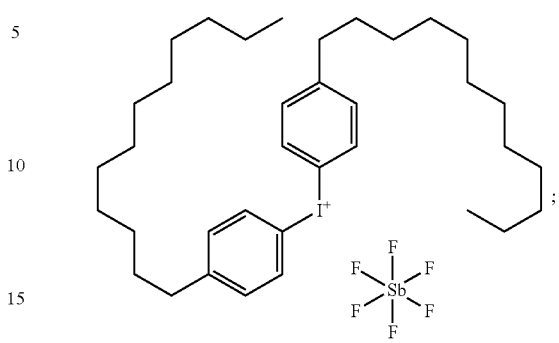

and
xi) combinations thereof. Combinations of the photoacid generators may be used as long as they are soluble in the selected solvent.

Examples of the first resin composition may be made by mixing the epoxy resin matrix with the free radical photoinitiator and the photoacid generator. In an example, a weight % ratio of the epoxy resin matrix to the free radical photoinitiator/photoacid generator combination ranges from about 99.8:0.2 to 90:10. In another example, a weight % ratio of the epoxy resin matrix to the free radical photoinitiator/photoacid generator combination ranges from about 98:2 to 95:5. In still another example, a weight % ratio of the epoxy resin matrix to the free radical photoinitiator/photoacid generator combination ranges from about 96:4 to 99:1. When lower amounts of the free radical photoinitiator/photoacid generator combination are included, the UV cure time may have to be increased to allow for complete reaction.

It is to be understood that the individual amounts of each of the epoxy resin matrix, the photoinitiator, and the photoacid generator may be higher or lower depending, at least in part, upon the epoxy resin matrix component(s).

Any example of the first resin composition may be made by mixing the epoxy resin matrix component(s) with the photoinitiator and the photoacid generator. In order to deposit the resin composition, these components (the epoxy resin matrix component(s), the photoinitiator and the photoacid generator) may be diluted in a suitable solvent (to achieve a desired viscosity for the deposition technique used), such as propylene glycol monomethyl ether acetate (PGMEA), toluene, dimethyl sulfoxide (DMSO), tetrahydrofuran (THF), etc. In an example, the concentration of the epoxy resin matrix in the solvent ranges from about 15 weight % (wt %) to about 56 wt %, and the concentration of the photoinitiator and the photoacid generator combination in the solvent ranges from about 1 wt % to about 10 wt %, although it is believed that the upper limits may be higher depending upon the respective solubility of the epoxy resin matrix and photoinitiator/photoacid generator in the solvent that is selected. In an example, the solvent is PGMEA. The total concentration (including the epoxy resin matrix, the photoinitiator, and the photoacid generator (and a polyacrylate or surfactant, if used)) of the final resin composition may range from about 16 wt % to about 66 wt %. The amount of solvent may range from about 34 wt % to about 84 wt %.

In some examples, the epoxy resin matrix of this example resin composition may also include an epoxy silane. The epoxy silane may be a support (or substrate)-bound epoxy silane. As an example, the substrate-bound epoxy silane may have the structure Substrate-O—Si(R)$_2$—O—C$_{2-6}$alkyl-(epoxide), where each R is an alkyl group, such as a methyl or ethyl group. In these examples, the resin composition 14 may be formed by mixing the support-bound epoxy with one or two different epoxies disclosed herein, along with the photoinitiator and the photoacid generator.

Some examples of the first resin composition may further include a dark quencher or an electron acceptor. A dark quencher is a substance that absorbs light energy from a fluorophore and dissipates the energy as heat. This provides a non-radiative route for relaxation of excited state species. In the examples disclosed herein, the dark quencher selected should be capable absorbing blue and/or green autofluorescence from the cured resin composition. An electron acceptor can also induce fluorescence quenching.

In an example, the dark quencher may comprise azo-dyes. In a further example, the dark quencher comprises a substituted azobenzene derivative selected from the group consisting of: 4-dimethylaminoazobenzene-4'-carboxylic acid:

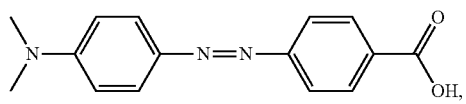 [SMILES: CN(C)c1ccc(N=Nc2ccc(C(=O)O)cc2)cc1]

dabcyl azide:

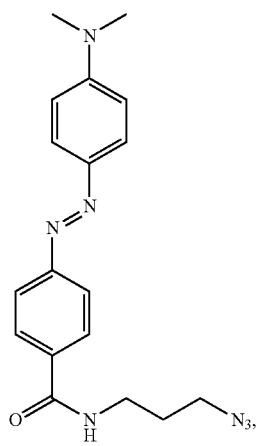 [SMILES: CN(C)c1ccc(/N=N/c2ccc(C(=O)NCCCN=[N+]=[N-])cc2)cc1]

dabsyl-azide:

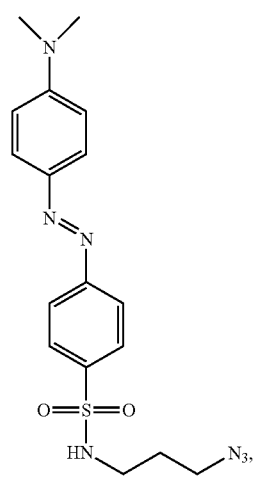 [SMILES: CN(C)c1ccc(/N=N/c2ccc(S(=O)(=O)NCCCN=[N+]=[N-])cc2)cc1]

disperse red 19:

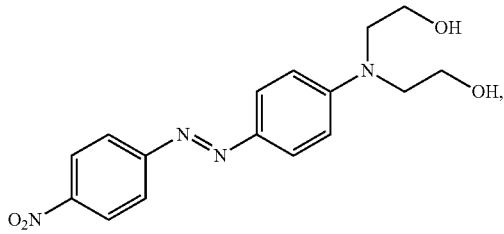 [SMILES: O=[N+]([O-])c1ccc(/N=N/c2ccc(N(CCO)CCO)cc2)cc1]

carbon black pigment (CBP) additives, a black dye-based quencher (such as, e.g., TRUEBLACK® lipofuscin autofluorescence quencher, 20× in DMF), and combinations thereof. Examples of suitable electron acceptors may include [5,6]-fullerene-C70:

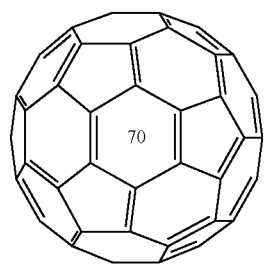 [SMILES: c1c2c3c4c(cc5c6c4c4c7c3c3c1Cc1cc8cc9cc%10cc(c%11c%10c%10c9c9c8c1c3c7c9c%10c4c%116)C5)C2]

or fullerene-C60:

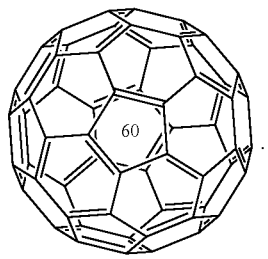 [SMILES: c12c3c4c5c1c1c6c7c2c2c8c3c3c9c4c4c%10c5c5c1c1c6c6c%11c7c2c2c7c8c3c3c8c9c4c4c9c%10c5c5c1c1c6c6c%11c2c2c7c3c3c8c4c4c9c5c1c1c6c2c3c41]

In an example, the dark quencher or electron acceptor may be present in an amount ranging from about 0.1 wt % to about 10 wt %, based on a total weight of the first resin composition.

Some other examples of the first resin composition may further include a polyacrylate or a surfactant. An example of a commercially available polyacrylate is BYK®-350 (available from BYK Additives & Instruments). Any biocompatible surfactant may be used, such as TWEEN® surfactants (e.g., polyethylene sorbitol esters (TWEEN® 80) and polyoxyethylene sorbitol esteris (TWEEN® 20) from Uniqema Americas LLC); TRITON™ X-100 (Octylphenol Ethoxylate from The Dow Chemical Co.), and polymeric surfactants available from BYK Additives and Instruments. In an example, the polyacrylate or surfactant may be present in the resin composition in an amount ranging from about 0.4 wt % total solids to about 1.6 wt % total solids.

Still some other examples of the first resin composition may further include, in addition to the epoxy resin matrix, photoinitiator, and photoacid generator, a free radical curable resin matrix which includes an acrylate group and a siloxane group. The curing mechanism of the acrylate groups of this resin matrix is orthogonal to the curing mechanism of the epoxy groups of the epoxy resin matrix, and thus it is believed that these components may be mixed without deleteriously affecting the curing efficiency. For example, some of free radicals generated by the photoinitiator disclosed herein may cure the free radical curable resin matrix, while others can initiate acid generation from the photoacid, which may cure the epoxy resin matrix.

When included, the free radical curable resin matrix may be present in an amount of 1 wt % to about 50 wt % of the total first resin composition.

In an example, the molecular weight of the acrylate monomer(s) of the free radical curable resin matrix may range from about 0.5 kDa to about 5 kDa, or from about 1 kDa to about 4.5 kDa. The cross linking functionality, and in turn, the cross linking density, depends on the number of arms (e.g., di, tri, tetra) of the monomer.

Examples of the free radical curable resin matrix are matrices comprising an acrylate selected from the group consisting of:

i) 1,3-bis(3-methacryloxypropyl) tetramethyldisiloxane:

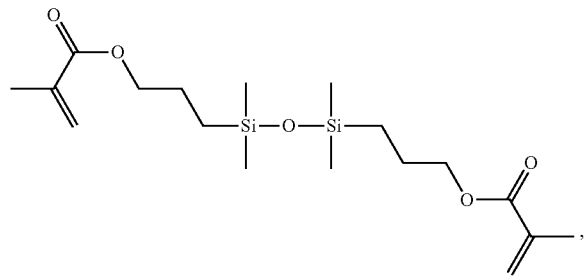 [SMILES: C=C(C)C(=O)OCCC[Si](C)(C)O[Si](C)(C)CCCOC(=O)C(=C)C]

ii) methacryloxypropyl-terminated polydimethylsiloxane:

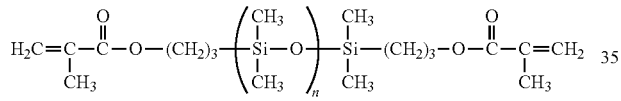

(wherein n ranges from 1 to 1000, or any range in between, for example, from 1 to 500, or 1 to 100, or 2 to 50, 1 to 10, 1 to 2, etc), iii) tetramethyl tetrakis[3-acryloxypropyl]cyclotetrasiloxane:

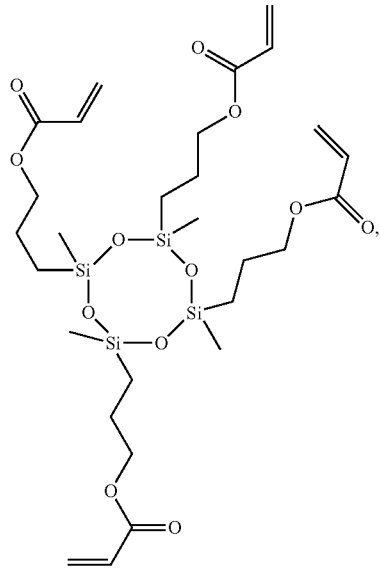 [SMILES: C=CC(=O)OCCC[Si]1(C)O[Si](C)(CCCOC(=O)C=C)O[Si](C)(CCCOC(=O)C=C)O[Si](C)(CCCOC(=O)C=C)O1]

iv) methacryl polyhedral oligomeric silsesquioxane (POSS):

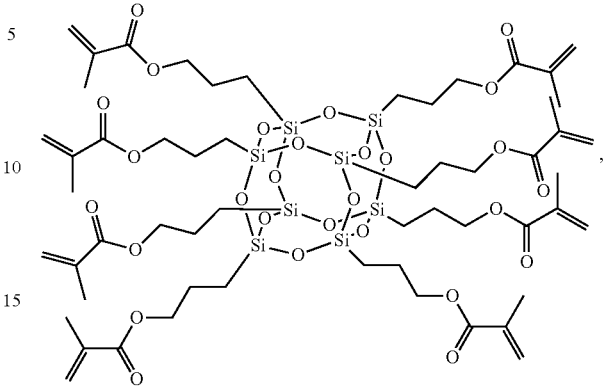

v) acrylo polyhedral oligomeric silsesquioxane:

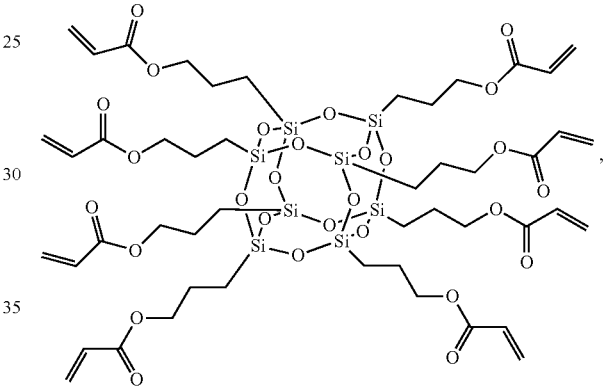

vi) acryloxypropyl methylsiloxane homopolymer:

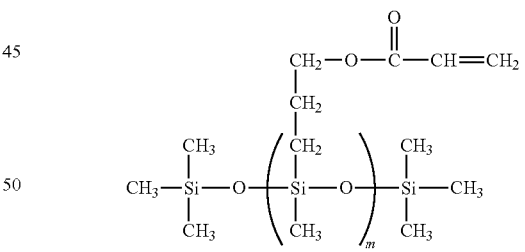

(wherein m ranges from 1 to 1000 or any range in between, for example, 1 to 500, 30 to 200, 30 to 100, etc.), and vii) combinations thereof. When combinations are used, it is to be understood that any two or more of the listed free radical curable resin matrices may be used together in the examples of the first resin composition as long they both are soluble in the solvent used in the first resin composition.

When any of the dark quencher or electron acceptor, the polyacrylate surface additive, and/or the free radical curable resin matrix is included, these components may be added to the other components and mixed to form other examples of the first resin composition.

Second Example Resin Composition

In some other examples disclosed herein, the resin complex includes an epoxy resin matrix including at least two different epoxy functionalized oligomeric silsesquioxanes, and a direct photoacid generator selected from the group consisting of diaryliodonium hexafluorophosphate, diaryliodonium hexafluoroantimonate, and (cumene)cyclopentadienyliron (II) hexafluorophosphate; wherein, when cured, the resin composition has low or no autofluorescence when exposed to blue excitation wavelengths ranging from about 380 nm to about 480 nm or green excitation wavelengths ranging from about 510 nm to about 560 nm.

In examples of the second resin composition, it is to be understood that any of the epoxy functionalized oligomeric silsesquioxanes described herein in reference to the first resin composition may be used, as long as two different epoxy POSS compounds are combined. In an example, the two different epoxy POSS compounds include glycidyl functionalized POSS and epoxycyclohexyl ethyl functionalized POSS.

The direct photoacid generator does not require a photoinitiator to initiate its decomposition, and thus can directly generate a superacid, which, in turn, initiates the polymerization and/or crosslinking of the epoxy resin matrix component(s). In the examples of the second resin composition disclosed herein, the direct photoacid generator is selected from the group consisting of:
i) diaryliodonium hexafluorophosphate:

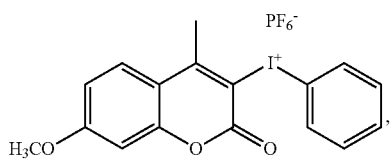

ii) diaryliodonium hexafluoroantimonate:

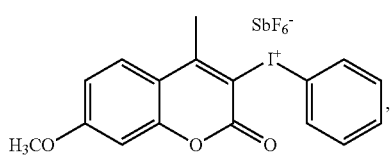

iii) (cumene)cyclopentadienyliron (II) hexafluorophosphate:

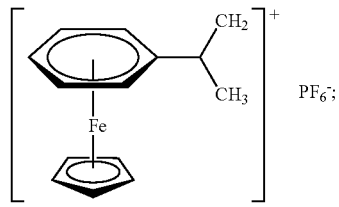

and
iv) combinations thereof. When combinations are used, it is to be understood that any two or more of the listed director photoacid generators may be used together in the examples of the second resin composition as long they both are soluble in the solvent used in the second resin composition.

Examples of the second resin composition may be made by mixing the epoxy resin matrix with the direct photoacid generator. In an example, a weight % ratio of the epoxy resin matrix to the direct photoacid generator ranges from about 99.8:0.2 to 90:10. In another example, a weight % ratio of the epoxy resin matrix to the direct photoacid generator ranges from about 98:2 to 95:5. In still another example, a weight % ratio of the epoxy resin matrix to the direct photoacid generator ranges from about 96:4 to 99:1. When lower amounts of the direct photoacid generator are included, the UV cure time may have to be increased to allow for complete reaction.

In order to deposit the second resin composition, these components (the epoxy resin matrix and the direct photoacid generator) may be diluted in a suitable solvent (to achieve a desired viscosity for the deposition technique used), such as propylene glycol monomethyl ether acetate (PGMEA), toluene, DMSO, THF, etc. In an example, the concentration of the epoxy resin matrix in the solvent ranges from about 15 wt % to about 56 wt %, and the concentration of the direct photoacid generator in the solvent ranges from about 1 wt % to about 10 wt % although it is believed that the upper limits may be higher depending upon the respective solubility of the epoxy resin matrix and direct photoacid generator in the solvent that is selected. In an example, the solvent is PGMEA. The total concentration (including the epoxy resin matrix, and the direct photoacid generator (and a polyacrylate or surfactant, if used)) of the final resin composition may range from about 16 wt % to about 66 wt %. The amount of solvent may range from about 34 wt % to about 84 wt %.

In some examples, the epoxy resin matrix of this example resin composition may also include an epoxy silane. The epoxy silane may be a support (or substrate)-bound epoxy silane. As an example, the substrate-bound epoxy silane may have the structure Substrate-O—Si(R)$_2$—O—C$_{2-6}$alkyl-(epoxide), where each R is an alkyl group, such as a methyl or ethyl group. In these examples, the resin composition may be formed by mixing the support-bound epoxy with at least two different epoxy functionalized oligomeric silsesquioxanes and the direct photoacid generator.

Some other examples of the second resin composition may further include the polyacrylate and/or the surfactants and/or the dark quencher and/or the electron acceptor described herein for the first example resin composition.

Flow Cell and Method

Any example of the resin composition disclosed herein may be used in the formation of the flow cell.

An example of a method 100 for making an example of a flow cell with the first resin composition is shown in FIG. 1. As shown, one example of the method 100 includes depositing a resin composition on a substrate, the resin composition including an epoxy resin matrix, a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide, and a photoacid generator (reference numeral 102); nanoimprinting the deposited resin composition using a working stamp (reference numeral 104); and curing the deposited resin composition to form a cured, patterned resin, wherein the cured, patterned resin has low or no autofluorescence when exposed to blue excitation wavelengths ranging from about 380 nm to about 480 nm or green excitation wavelengths ranging from about 510 nm to about 560 nm (reference numeral 106). The resulting flow cell includes a substrate and a cured, patterned resin on the substrate, the cured, patterned resin including depressions separated by interstitial regions, and the cured, patterned resin having been formed from an example of the first resin composition, which includes the epoxy resin matrix, the free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide, and the photoacid generator.

Figure 2:
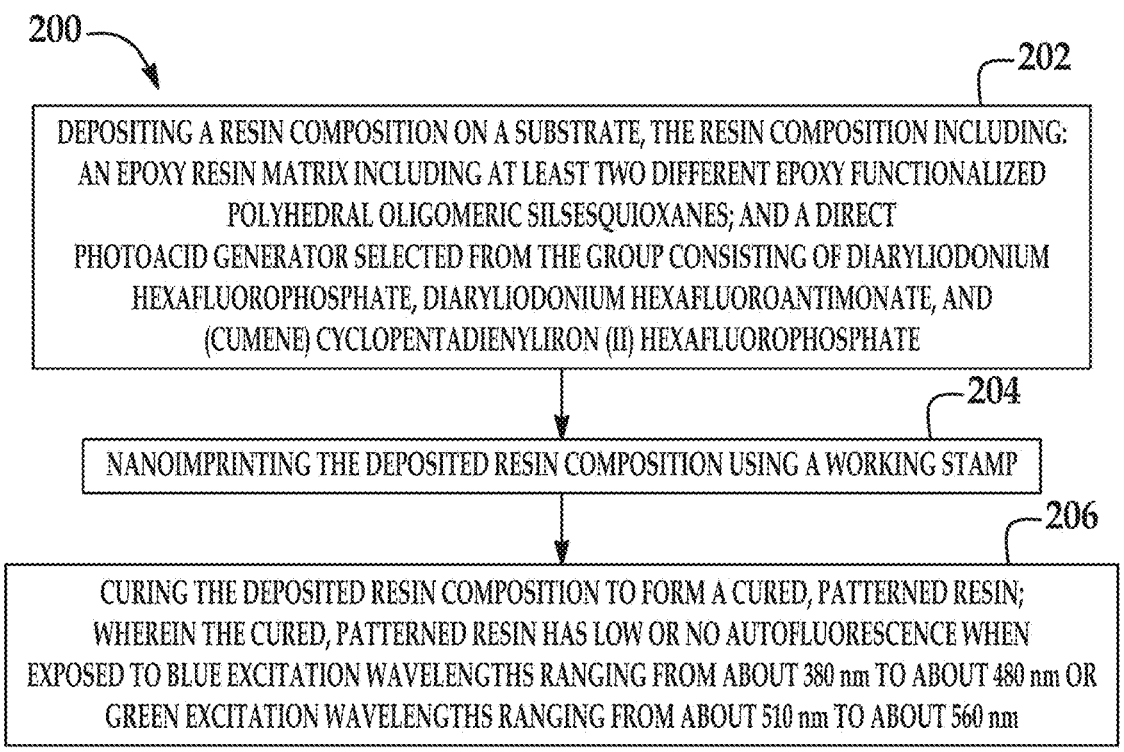
FIG. 2 is a flow diagram illustrating another example of a method disclosed herein.

Another example of a method 200 for making another example of a flow cell with the second resin composition is shown in FIG. 2. As shown, one example of the method 200 includes depositing a resin composition on a substrate, the resin composition including an epoxy resin matrix including at least two different epoxy functionalized polyhedral oligomeric silsesquioxanes; and a direct photoacid generator selected from the group consisting of diaryliodonium hexafluorophosphate, diaryliodonium hexafluoroantimonate, and (cumene)cyclopentadienyliron (II) hexafluorophosphate (reference numeral 202); nanoimprinting the deposited resin composition using a working stamp (reference numeral 204); and curing the deposited resin composition to form a cured, patterned resin, wherein the cured, patterned resin has low or no autofluorescence when exposed to blue excitation wavelengths ranging from about 380 nm to about 480 nm or green excitation wavelengths ranging from about 510 nm to about 560 nm (reference numeral 206). The resulting flow cell includes a substrate and a cured, patterned resin on the substrate, the cured, patterned resin including depressions separated by interstitial regions, and the cured, patterned resin having been formed from an example of the second resin composition, which includes the epoxy resin matrix including at least two different epoxy functionalized polyhedral oligomeric silsesquioxanes; and the direct photoacid generator selected from the group consisting of diaryliodonium hexafluorophosphate, diaryliodonium hexafluoroantimonate, and (cumene) cyclopentadienyliron (II) hexafluorophosphate.

While not shown in FIGS. 1 and 2, examples of the method 100, 200 may further include applying a polymer coating in the depressions, and grafting a primer to the polymer coating. The methods 100, 200, including these additional processes, will now be described further in reference to FIGS. 3A through 3E.

FIG. 3A depicts a substrate 12, and FIG. 3B depicts a resin composition 14 deposited on the substrate 12.

Examples of suitable substrate 12 include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The substrate 12 may also be glass or silicon, with a coating layer of tantalum oxide or another ceramic oxide at the surface.

Some examples of the substrate 12 may have a surface-bound epoxy silane attached thereto, which can react with the other resin composition components to form the resin composition 14 (and the cured resin composition 14) on the substrate 12.

In an example, the substrate 12 may have a diameter ranging from about 2 mm to about 300 mm, or a rectangular sheet or panel having its largest dimension up to about 10 feet (~3 meters). In an example, the substrate 12 is a wafer having a diameter ranging from about 200 mm to about 300 mm. In another example, the substrate 12 is a die having a width ranging from about 0.1 mm to about 10 mm. While example dimensions have been provided, it is to be understood that a substrate 12 with any suitable dimensions may be used. For another example, a panel may be used that is a rectangular substrate 12, which has a greater surface area than a 300 mm round wafer.

The resin composition 14 may be any examples of the resin composition described herein (e.g., examples of the first resin composition or examples of the second resin composition), which includes the photoinitiator package or the direct photoacid generator. The resin composition 14 may be deposited on the substrate 12 suing any suitable application technique, which may be manual or automated. As examples, the deposition of the resin composition 14 may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, aerosol printing, screen printing, microcontact printing, inkjet printing, or the like. In one example, spin coating is used.

The deposited resin composition 14 is then patterned, using any of the patterning techniques mentioned herein. In the example shown in FIG. 3B, nanoimprint lithography is used to pattern the resin composition 14. After the resin composition 14 is deposited, it may be softbaked to remove excess solvent. A nanoimprint lithography mold or working stamp 20 is pressed against the layer of the resin composition 14 to create an imprint on the resin composition 14. In other words, the resin composition 14 is indented or perforated by the protrusions of the working stamp 20. The resin composition 14 may be then be cured with the working stamp 20 in place. For the resin compositions 14 disclosed herein, curing may be accomplished by exposure to actinic radiation, such as ultraviolet (UV) radiation. In examples in which the first resin composition is used, curing promotes radical formation due to the presence of the photoinitiator, and these radicals are used to decompose the photoacid generator into a superacid that initiates polymerization and/or cross-linking of the epoxy resin matrix. In some examples of the first resin composition, the radical formation also cures the acrylate portion of the resin composition. In examples in which the second resin composition is used, curing promotes decomposition of the direct photoacid generator into a superacid that initiates polymerization and/or cross-linking of the epoxy resin matrix. In any of the examples disclosed herein, curing promotes polymerization and/or cross-linking of the resin compositions 14. As an example, curing may include a single UV exposure stage, or may include multiple stages, including a softbake (e.g., to drive off solvent(s)) and, in some instances, a hardbake. When included, the softbake may take place after the resin is deposited and before the working stamp 20 is positioned therein, and at a lower temperature, ranging from about 50° C. to about 150° C., for greater than 0 seconds to about 3 minutes. In an example, the softbake time ranges from about 30 seconds to about 2.5 minutes. During the softbake, one or more chemical processes may be taking place that further contribute to a reduction in the autofluorescence. Example chemical processes may include evaporation of some of resin composition material(s), sublimation of some of resin composition material(s), polymerization of some of the resin composition material(s), and/or combinations thereof. The working stamp 20 is released/detached before the hardbake (if performed), e.g., so that the working stamp 20 does not bond to the cured resin composition 14. The duration of the hardbake may last from about 5 seconds to about 10 minutes at a temperature ranging from about 100° C. to about 300° C. Hardbaking may be performed, for example, to remove residual solvent(s) from the resin composition 14, to further polymerization of some of the resin composition material(s) (and thus enhance the extent of curing), and/or to further reduce the autofluorescence. Examples of devices that can be used for softbaking and/or hardbaking include a hot plate, oven, etc.

After the release of the working stamp 20, topographic features, e.g., the depressions 16, are in the resin composition 14. As shown in FIG. 3C, the resin composition 14 having the depressions 16 defined therein is referred to as the cured, patterned resin 14'. The cured, patterned resin 14' may be subject to further hard baking to complete the cure and to lock in the imprinted topography. In some examples, the additional hard baking may be performed at a temperature ranging from about 60° C. to about 300° C.

The chemical make-up of the cured, patterned resin 14' depends upon whether the first resin composition or the second resin composition is used. The chemical make-up of the cured, patterned resin 14' formed from the first resin composition depends upon the epoxy resin matrix or matrices, the photoinitiator, and the photoacid generator, and in some instances the free radical curable resin component, used in the first resin composition. The chemical make-up of the cured, patterned resin 14' formed from the second resin composition depends upon the at least two different epoxy POSS compounds and the direct photoacid generator used in the second resin composition.

As shown in FIG. 3C, the cured, patterned resin 14' includes the depressions 16 defined therein, and interstitial regions 22 separating adjacent depressions 16. In the examples disclosed herein, the depressions 16 become functionalized with a polymer coating 18 (FIGS. 3C-3D) and primers 24 (FIGS. 3E-3F), while portions of the interstitial regions 22 may be used for bonding but will not have the polymer coating 18 or the primer(s) 24 thereon.

Many different layouts of the depressions 16 may be envisaged, including regular, repeating, and non-regular patterns. In an example, the depressions 16 are disposed in a hexagonal grid for close packing and improved density. Other layouts may include, for example, rectilinear (i.e., rectangular) layouts (e.g., lines or trenches), triangular layouts, and so forth. In some examples, the layout or pattern can be an x-y format of depressions 16 that are in rows and columns. In some other examples, the layout or pattern can be a repeating arrangement of depressions 16 and/or interstitial regions 22. In still other examples, the layout or pattern can be a random arrangement of depressions 16 and/or interstitial regions 22. The pattern may include spots, pads, wells, posts, stripes, swirls, lines, triangles, rectangles, circles, arcs, checks, plaids, diagonals, arrows, squares, and/or cross-hatches. In an example, the depressions 16 are wells, as shown in FIG. 3C.

The layout or pattern may be characterized with respect to the density of the depressions 16 (i.e., number of depressions 16) in a defined area. For example, the depressions 16 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$ about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of depressions 16 in the cured, patterned resin' 14 can be between one of the lower values and one of the upper values selected from the ranges above. As examples, a high density array may be characterized as having depressions 16 separated by less than about 100 nm, a medium density array may be characterized as having depressions 16 separated by about 400 nm to about 1 µm, and a low density array may be characterized as having depressions 16 separated by greater than about 1 µm. While example densities have been provided, it is to be understood that substrates with any suitable densities may be used.

The layout or pattern of the depressions 16 may also or alternatively be characterized in terms of the average pitch, i.e., the spacing from the center of the depression 16 to the center of an adjacent depression 16 (center-to-center spacing) or from the edge of one depression 16 to the edge of an adjacent depression 16 (edge-to-edge spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 µm, about 0.5 µm, about 1 µm, about 5 µm, about 10 µm, about 100 µm, or more. Alternatively or additionally, the average pitch can be, for example, at most about 100 µm, about 10 µm, about 5 µm, about 1 µm, about 0.5 µm, about 0.1 µm, or less. The average pitch for a particular pattern of depressions 16 can be between one of the lower values and one of the upper values selected from the ranges above. In an example, the depressions 16 have a pitch (center-to-center spacing) of about 1.5 µm. While example average pitch values have been provided, it is to be understood that other average pitch values may be used.

In the example shown in FIGS. 3A through 3E, the depressions 16 are wells, and thus the cured, patterned resin 14' includes an array of wells in a surface thereof. The wells may be micro wells or nanowells. The size of each well may be characterized by its volume, well opening area, depth, and/or diameter.

Each well can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1 \times 10^{-3}$ µm$^3$, about $1 \times 10^{-2}$ µm$^3$, about 0.1 µm$^3$, about 1 µm$^3$, about 10 µm$^3$, about 100 µm$^3$, or more. Alternatively or additionally, the volume can be at most about $1 \times 10^4$ µm$^3$, about $1 \times 10^3$ µm$^3$, about 100 µm$^3$, about 10 µm$^3$, about 1 µm$^3$, about 0.1 µm$^3$, or less. It is to be understood that the polymer coating 18 can fill all or part of the volume of a well.

The area occupied by each well opening on a surface can be selected based upon similar criteria as those set forth above for well volume. For example, the area for each well opening on a surface can be at least about $1 \times 10^{-3}$ µm$^2$, about $1 \times 10^{-2}$ µm$^2$, about 0.1 µm$^2$, about 1 µm$^2$, about 10 µm$^2$, about 100 µm$^2$, or more. Alternatively or additionally, the area can be at most about $1 \times 10^3$ µm$^2$, about 100 µm$^2$, about 10 µm$^2$, about 1 µm$^2$, about 0.1 µm$^2$, about $1 \times 10^{-2}$ µm$^2$, or less. The area occupied by each well opening can be greater than, less than or between the values specified above.

The depth of each well can be at least about 0.1 µm, about 1 µm, about 10 µm, about 100 µm, or more. Alternatively or additionally, the depth can be at most about $1 \times 10^3$ µm, about 100 µm, about 10 µm, about 1 µm, about 0.1 µm, or less. The depth of each well can be greater than, less than or between the values specified above.

In some instances, the diameter of each well can be at least about 50 nm, about 0.1 µm, about 0.5 µm, about 1 µm, about 10 µm, about 100 µm, or more. Alternatively or additionally, the diameter can be at most about $1 \times 10^3$ µm, about 100 µm, about 10 µm, about 1 µm, about 0.5 µm, about 0.1 µm, or less (e.g., about 50 nm). The diameter of each well can be greater than, less than or between the values specified above.

As shown between FIGS. 3C and 3D, after the resin composition 14 is patterned and cured, the cured, patterned resin 14' may be treated to prepare the surface for application of a polymer coating 18.

In an example, the cured, patterned resin 14' may be exposed to silanization, which attaches a silane or the silane derivative to the cured, patterned resin 14'. Silanization introduces the silane or the silane derivative across the surface, including in the depressions 16 (e.g., on the bottom surface and along the side walls) and on the interstitial regions 22.

Silanization may be accomplished using any silane or silane derivative. The selection of the silane or silane derivative may depend, in part, upon the functionalized molecule that is to be used to form the polymer coating 18 (shown in FIG. 3D), as it may be desirable to form a covalent bond between the silane or silane derivative and the polymer coating 18. The method used to attach the silane or silane derivative to the cured, patterned resin 14' may vary depending upon the silane or silane derivative that is being used. Several examples are set forth herein.

In an example, the silane or silane derivative is (3-aminopropyl)triethoxysilane (APTES) or 3-aminopropyl)trimethoxysilane (APTMS) (i.e., $X-R^B-Si(OR^C)_3$, wherein X is amino, $R^B$ is $-(CH_2)_3-$, and $R^C$ is ethyl or methyl). In this example, the substrate 12 surface may be pre-treated with the (3-aminopropyl)triethoxysilane (APTES) or 3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm² to 30 J/cm² of energy generates an active nitrene species, which can readily undergo a variety of insertion reactions with PAZAM (e.g., one example of the functionalized molecule used to form the polymer coating 18).

Other silanization methods may also be used. Examples of suitable silanization methods include vapor deposition (e.g., a YES method), spin coating, or other deposition methods. Some examples of methods and materials that may be used to silanize cured, patterned resin 14' are described herein, although it is to be understood that other methods and materials may be used.

In an example utilizing the YES CVD oven, the cured, patterned resin 14' on the substrate 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative (e.g., liquid norbornene silane) may be deposited inside a glass vial and placed inside a glass vacuum desiccator with a patterned substrate 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivatives, such as those silane or silane derivative including a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1 (8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted with any of the R groups described herein.

The attachment of the silane or silane derivative forms a pre-treated (e.g., silanized) cured, patterned resin 14', which includes silanized depressions and silanized interstitial regions.

In other examples, the cured, patterned resin 14' may not be exposed to silanization. Rather, the cured, patterned resin 14' may be exposed to plasma ashing, and then the polymer coating 18 may be directly spin coated (or otherwise deposited) on the plasma ashed cured, patterned resin 14'. In this example, plasma ashing may generate surface-activating agent(s) (e.g., hydroxyl (C—OH or Si—OH) and/or carboxyl groups) that can adhere the polymer coating 18 to the cured, patterned resin 14'. In these examples, the polymer coating 18 is selected so that it reacts with the surface groups generated by plasma ashing.

In still other examples, the cured, patterned resin 14' may include unreacted epoxy groups; and thus may not be exposed to silanization because the unreacted epoxy groups can react directly with amino functional groups of the polymer coating 18. In this example, plasma ashing may be performed, e.g., if it is desirable to clean the surface of potential contaminants.

The polymer coating 18 may then be applied to the pre-treated cured, patterned resin 14' (as shown between FIGS. 3C and 3C). The polymer coating 18 may be a semi-rigid polymeric material that is permeable to liquids and gases and that is tethered to the cured, patterned resin 14'.

An example of the polymer coating 18 includes an acrylamide copolymer, such as poly(N-(5-azidoacetamidylpentyl)acrylamide-co-acrylamide, PAZAM. PAZAM and some other forms of the acrylamide copolymer are represented by the following structure (I):

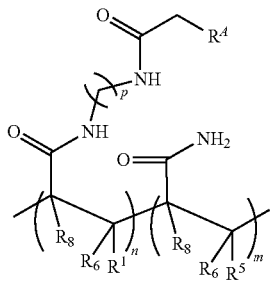

wherein:
R$^1$ is H or optionally substituted alkyl;
R$^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
R$^5$, R$_6$, and R$_8$ are each independently selected from the group consisting of H and optionally substituted alkyl;
each of the —(CH$_2$)$_p$— can be optionally substituted;
p is an integer in the range of 1 to 50;
n is an integer in the range of 1 to 50,000; and
m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the polymer coating 18 may be a variation of the structure (I). In one example, the acrylamide unit may be replaced with N,N-dimethylacrylamide

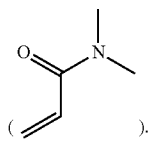

In this example, the acrylamide unit in structure (I) may be replaced with

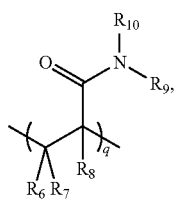

where R$_6$, R$_7$, and R$_8$ are each H, and R$_9$ and R$_{10}$ are each a methyl group (instead of H as is the case with the acrylamide). In this example, q may be an integer in the range of 1 to 100,000. In another example, the N,N-dimethylacrylamide may be used in addition to the acrylamide unit. In this example, structure (I) may include

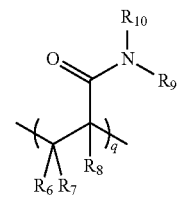

in addition to the recurring "n" and "m" features, where R$_6$, R$_7$, and R$_8$ are each H, and R$_9$ and R$_{10}$ are each a methyl group. In this example, q may be an integer in the range of 1 to 100,000.

As another example polymer, the recurring "n" feature in structure (I) may be replaced with a monomer including a heterocyclic azido group having structure (II):

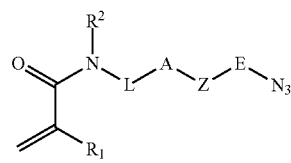

wherein R$^1$ is H or C1-C4 alkyl; R$_2$ is H or C1-C4 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or C1-C4 alkyl attached to the N; and Z is a nitrogen containing heterocycle. Examples of Z include 5 to 10 ring members present as a single cyclic structure or a fused structure.

As still another example, the polymer may include a recurring unit of each of structure (III) and (IV):

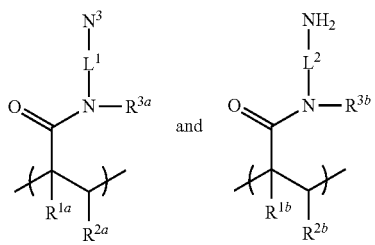

wherein each of R$^{1a}$, R$^{2a}$, R$^{1b}$ and R$^{2b}$ is independently selected from hydrogen, optionally substituted alkyl or optionally substituted phenyl; each R$^{3a}$ and R$^{3b}$ is independently selected from hydrogen, optionally substituted alkyl, optionally substituted phenyl, or optionally substituted C7-C14 aralkyl; and each L$^1$ and L$^2$ is independently selected from an optionally substituted alkylene linker or an optionally substituted heteroalkylene linker.

It is to be understood that other functionalized molecules may be used to form the polymer coating 18, as long as they are functionalized to interact with the pre-treated cured, patterned resin 14' and the subsequently applied primer(s) 24. Other examples of suitable molecules for forming the polymer coating 18 include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable molecules for forming the polymer coating 18 include mixed copolymers of acrylamides and acrylates. Branched polymers, such as star polymers, star-shaped or star-block polymers, dendrimers, and the like may also be used.

The functionalized molecule (e.g., PAZAM) may be deposited on the surface of the pre-treated cured, patterned resin 14' using spin coating, or dipping or dip coating, or flow of the functionalized molecule under positive or negative pressure, or another suitable technique. The functionalized molecule may be present in a mixture. In an example, the mixture includes PAZAM in water or in an ethanol and water mixture.

After being coated, the functionalized molecule may also be exposed to a curing process to form the polymer coating 18 across the entire patterned substrate (i.e., in depression(s) 16 and on interstitial region(s) 22). In an example, curing the functionalized molecule may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The attachment of the polymer coating 18 to the pre-treated depressions and interstitial regions may be through covalent bonding. The covalent linking of the polymer coating 18 to the silanized or plasma ashed depressions is helpful for maintaining the polymer coating 18 in the depressions 16 throughout the lifetime of the ultimately formed flow cell during a variety of uses. The following are some examples of reactions that can take place between the silane or silane derivative and the polymer coating 18.

When the silane or silane derivative includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative includes a bicyclononyne as the unsaturated moiety, the bicyclononyne can undergo similar SPAAC alkyne cycloaddition with azides or nitrile oxides attached to PAZAM due to the strain in the bicyclic ring system.

To form the polymer coating 18 in the depression(s) 16 and not on the interstitial region(s) 22 of the cured, patterned resin 14', the polymer coating 18 may be polished off of the interstitial regions 22. The polishing process may be performed with a gentle chemical slurry (including, e.g., an abrasive, a buffer, a chelating agent, a surfactant, and/or a dispersant) which can remove the polymer coating 18 from the interstitial regions 22 without deleteriously affecting the underlying cured, patterned resin 14' and/or substrate 12 at those regions. Alternatively, polishing may be performed with a solution that does not include the abrasive particles. The chemical slurry may be used in a chemical mechanical polishing system. In this example, polishing head(s)/pad(s) or other polishing tool(s) is/are capable of polishing the polymer coating 18 from the interstitial regions 22 while leaving the polymer coating 18 in the depressions 16 and leaving the underlying cured, patterned resin 14' at least substantially intact. As an example, the polishing head may be a Strasbaugh ViPRR II polishing head. In another example, polishing may be performed with a polishing pad and a solution without any abrasive. For example, the polish pad may be utilized with a solution free of the abrasive particle (e.g., a solution that does not include abrasive particles).

FIG. 3D depicts the flow cell precursor 10 after the polymer layer 18 has been applied to the depressions 16. The flow cell precursor 10 may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

As shown between FIGS. 3D and 3E, a grafting process is performed in order to graft a primer 24 to the polymer coating 18 in the depression(s) 16. The primer 24 may be any forward amplification primer or reverse amplification primer that includes an alkyne functional group, or another terminated primer. Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. A mixture of primers may also be used. Specific examples of suitable primers include P5 and/or P7 primers, which are used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms.

In an example, grafting may be accomplished by flow through deposition (e.g., using a temporarily bound lid), dunk coating, spray coating, puddle dispensing, or by another suitable method that will attach the primer(s) 24 to the polymer coating 18. Each of these example techniques may utilize a primer solution or mixture, which may include the primer(s), water, a buffer, and a catalyst.

Dunk coating may involve submerging the flow cell precursor 10 (shown in FIG. 3D) into a series of temperature controlled baths. The baths may also be flow controlled and/or covered with a nitrogen blanket. The baths may include the primer solution or mixture. Throughout the various baths, the primer(s) 24 will attach to the primer-grafting functional group(s) of the polymer coating 18 in at least some of the depression(s) 16. In an example, the flow cell precursor 10 will be introduced into a first bath including the primer solution or mixture where a reaction takes place to attach the primer(s) 24, and then moved to additional baths for washing. Movement from bath to bath may involve a robotic arm or may be performed manually. A drying system may also be used in dunk coating.

Spray coating may be accomplished by spraying the primer solution or mixture directly onto the flow cell precursor 10. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the flow cell precursor 10. The applied primer solution or mixture may be applied to or spread across the entire surface of the flow cell precursor 10. The primer coated flow cell precursor 10 may be incubated for a time ranging from about 2 minutes to about 60 minutes at a temperature ranging from about 0° C. to about 80° C. After incubation, the primer solution or mixture may be diluted and removed using, for example, the spin coater.

FIG. 3F illustrates an example of the flow cell 10' after primer grafting. While a single type of primer 24 is shown, it is to be understood that two or more different primers 24 may be attached.

The examples shown in FIGS. 3E and 3F are examples of the flow cell 10' without a lid bonded thereto. While not shown, the flow cells 10' may have the lid bonded to at least a portion of the interstitial region 22. The lid may be bonded before or after primer 24 grafting. When the lid is performed prior to primer 24 grafting, it is to be understood that a flow through process may be used for grafting. In the flow through process, the primer solution or mixture may be introduced into a flow channel(s) (defined between the lid and the interstitial region 22) through respective input port(s) (not shown), may be maintained in the flow channel(s) for a time sufficient (i.e., an incubation period) for the primer(s) 24 to attach to the polymer coating 18 in one or more of the depressions 16 and then may be removed from respective output port(s) (not shown). After primer 24 attachment, the additional fluid(s) may be directed through the flow channel(s) to wash the now functionalized depressions and the flow channel(s).

The lid may be positioned on the interstitial region 22 so that it defines a single flow channel or multiple, fluidically separated flow channels.

The lid may be any material that is transparent to an excitation light that is directed toward the depression(s) 16. As examples, the lid may be glass (e.g., Corning Eagle XG (CEXG), borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid may be integrally formed with sidewall(s) that correspond with the shape of the portion of the interstitial region 22 to which it will be bonded. For example, a recess may be etched into a transparent block to form a substantially planar (e.g., top) portion and sidewall(s) extending from the substantially planar portion. When the etched block is mounted to the interstitial region 22, the recess may become the flow channel.

In other examples, the sidewall(s) and the lid may be separate components that are coupled to each other. For example, the lid may be a substantially rectangular block having an at least substantially planar exterior surface and an at least substantially planar interior surface that defines a portion (e.g., a top portion) of the flow channel (once bonded to the portion of the interstitial region 22). The block may be mounted onto (e.g., bonded to) the sidewall(s), which are bonded to the portion of the interstitial region 22 and form sidewall(s) of the flow channel. In this example, the sidewall(s) may include any of the materials set forth herein for the spacer layer (described below).

The lid may be bonded using any suitable technique, such as laser bonding, diffusion bonding, anodic bonding, eutectic bonding, plasma activation bonding, glass frit bonding, or others methods known in the art. In an example, a spacer layer may be used to bond the lid to the portion of the interstitial region 22. The spacer layer may be any material that will seal at least some of the interstitial regions 22 and the lid together.

In one example, the spacer layer may be a radiation-absorbing material that absorbs radiation at a wavelength that is transmitted by the lid and/or the cured, patterned resin 14'. The absorbed energy, in turn, forms the bond between the spacer layer and the lid and between the spacer layer and the cured, patterned resin 14'. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer is the radiation-absorbing material, the spacer layer may be positioned at an interface between the lid and the portion of the interstitial region 22 so that the spacer layer contacts the desired bonding region. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer may include a radiation-absorbing material in contact therewith. The radiation-absorbing material may be applied at the interface between the spacer layer and the lid as well as at the interface between the spacer layer and the portion of the interstitial region 22. As an example, the spacer layer may be polyimide and the separate radiation-absorbing material may be carbon black. In this example, the separate radiation-absorbing material absorbs the laser energy that forms the bonds between the spacer layer and the lid and between the spacer layer and the portion of the interstitial region 22. In this example, compression may be applied at the respective interfaces while laser energy at a suitable wavelength is applied to the interfaces (i.e., the radiation-absorbing material is irradiated).

The flow cells 10' disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques, since the polymer coating 18 and attached primer(s) 24 are present in the depressions 16 and not on the interstitial regions 22, amplification will be confined to the depressions.

As one example, a sequencing by synthesis (SBS) reaction may be run on a system such as the HISEQ™, HISEQX™, MISEQ™, MISEQDX™, MINISEQ™, NOVASEQ™, ISEQ™, NEXTSEQDX™, or NEXTSEQ™ sequencer systems from Illumina (San Diego, CA). In SBS, extension of a nucleic acid primer (e.g., a sequencing primer) along a nucleic acid template (i.e., the sequencing template) is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the sequencing primer (thereby extending the sequencing primer) in a template dependent fashion such that detection of the order and type of nucleotides added to the sequencing primer can be used to determine the sequence of the template.

Prior to sequencing, amplification primers 24 can be exposed to a sequencing library, which is amplified using any suitable method, such as cluster generation.

In one example of cluster generation, the library fragments are copied from the hybridized primers 24 by 3' extension using a high-fidelity DNA polymerase. The original library fragments are denatured, leaving the copies immobilized. Isothermal bridge amplification may be used to amplify the immobilized copies. For example, the copied templates loop over to hybridize to an adjacent, complementary primer 24, and a polymerase copies the copied templates to form double stranded bridges, which are denatured to form two single stranded strands. These two strands loop over and hybridize to adjacent, complementary primers 24 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template strands.

To initiate a first SBS cycle, one or more labeled nucleotides, DNA polymerase, etc., may be delivered into/through the flow channel, etc., where sequencing primer extension causes a labeled nucleotide to be incorporated to the template strands. This incorporation can be detected through an imaging event. During an imaging event, an illumination system (not shown) may provide an excitation light to the functionalized depressions. During the imaging event, any emissions (if any) from the cured, patterned resin 14' resulting from exposure to blue and/or green excitation wavelengths may be i) non-detected because they are below a threshold limit of detection, or ii) distinguished as noise due to the low autofluorescence of the cured, patterned resin 14'. As such, the cured, patterned resin 14' disclosed herein is essentially invisible to the detector.

In some examples, the nucleotides can further include a reversible termination property that terminates further primer extension once a nucleotide has been added to the sequencing primer. For example, a nucleotide analog having a reversible terminator moiety can be added to the sequencing primer such that subsequent extension cannot occur until a deblocking agent is delivered to remove the moiety. Thus, for examples that use reversible termination, a deblocking reagent can be delivered to the flow channel, etc. (before or after detection occurs).

Wash(es) may take place between the various fluid delivery steps. The SBS cycle can then be repeated n times to extend the sequencing primer by n nucleotides, thereby detecting a sequence of length n.

While SBS has been described in detail, it is to be understood that the flow cells described herein may be utilized with other sequencing protocol, for genotyping, or in other chemical and/or biological applications. Paired-end sequencing facilitates detection of genomic rearrangements and repetitive sequence elements, as well as gene fusions and novel transcripts. In another example, the flow cells disclosed herein may be used for on-cell library generation.

While the example described in FIGS. 1, 2, and 3A through 3F illustrate the use of the example resin compositions in the formation of a flow cell, it is to be understood that the resin compositions disclosed herein may be used in other applications where low autofluorescence is desired. As one example, the resin composition 14, 14' may be used in any optically-based SBS technique. As other examples, the resin composition 14, 14' may be used in planar waveguides, in complementary metal-oxide semiconductors (CMOS), etc.

To further illustrate the present disclosure, examples are given herein. It is to be understood that these examples are provided for illustrative purposes and are not to be construed as limiting the scope of the present disclosure.

EXAMPLES

Example 1

Seven examples of the resin compositions were prepared. Each example included a different epoxy resin matrix, which included glycidyl functionalized POSS; epoxycyclohexyl ethyl functionalized POSS; trimethylolpropane triglycidyl ether; tetrakis(epoxycyclohexyl ethyl)tetramethyl cyclotetrasiloxane; a copolymer of (epoxycyclohexylethyl)methylsiloxane and dimethylsiloxane; 1,3-bis[2-(3,4-epoxycyclohexyl) ethyl] tetramethyl disiloxane; or 1,3-bis (glycidoxypropyl)tetramethyl disiloxane. About 17 wt % of each of these epoxy resin matrices was respectively mixed with about 1.2 wt % total of a comparative photoinitiator/photoacid generator combination, namely thioxanth-9-one (ITX) (about 0.34 wt %) and TEGO® PC 1467 (Evonik Industries) (about 0.85 wt %), about 1.4 wt % polyacrylate (BYK®-350), and a solvent (PGMEA). The solvent made up the balance (about 80 wt %) of the composition. This photoinitiator/photoacid generator combination is considered a comparative combination because it exhibits high autofluorescence when exposed to blue and green excitation wavelengths. However, this example was performed to demonstrate the imprintability of the various epoxy resin matrices.

Each of these resin compositions was deposited by spin coating (at 2200 (revolutions per minute) rpm for about 1 minute) on a glass or silicon substrate. After deposition, the resin compositions were exposed to a softbake at about 120° C. for about 2 minutes to drive off PGMEA. The deposited resin composition was then imprinted using nanoimprint lithography. A working stamp was pressed into the deposited composition and the resin was exposed to UV curing with an LED UV lamp for about 20 seconds. Hard baking at 250° C. for about 10 minutes was also performed after the working stamp was removed.

Figure 4A:
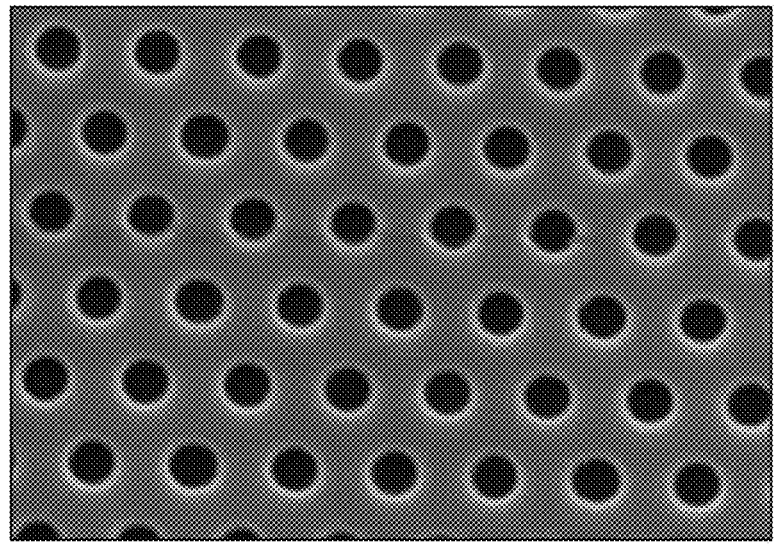
FIGS. 4A and 4B are scanning electron micrograph images of example wells formed using different examples of the resin compositions disclosed herein.
Figure 4B:
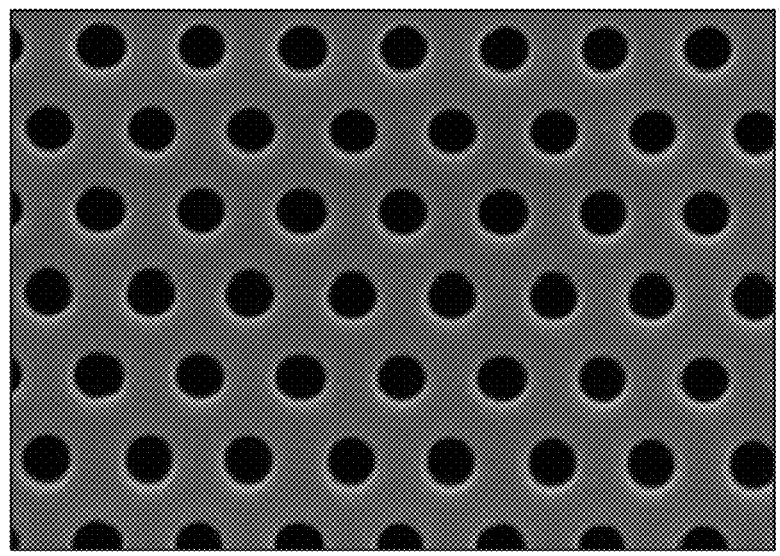

Each of the resins was successfully nanoimprinted. SEM images of two of the cured, patterned resins were taken. SEM images were not taken of the other cured, patterned resins. The images are shown in FIGS. 4A and 4B, respectively, for the cured, patterned resins formed with trimethylolpropane triglycidyl ether and tetrakis(epoxycyclohexyl ethyl)tetramethyl cyclotetrasiloxane. These images demonstrate that the epoxy resin matrices disclosed herein can be nanoimprinted to form suitable depressions for flow cells or other suitable applications. It is believed that the low autofluorescence will be achieved when the comparative photoinitiator/photoacid generator combination of this example is replaced with the photoinitiator/photoacid generator combination disclosed herein or the direct photoacid generator disclosed herein.

Example 2

Figure 5A:
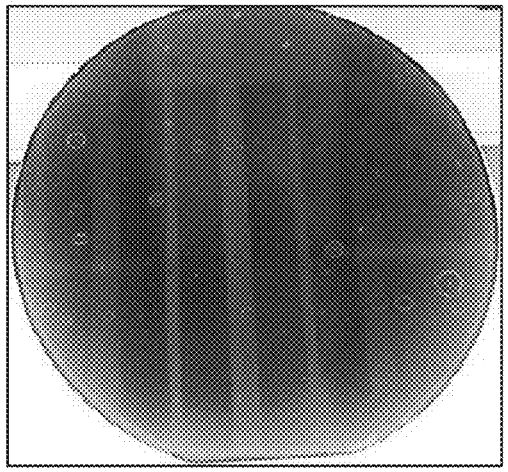
FIGS. 5A through 5D are black and white representations of originally colored photographs of, respectively, (FIG. 5A) an example of a cured and patterned first example resin composition, (FIG. 5B) an example of a cured and patterned second example resin composition, (FIG. 5C) an example of a cured and patterned first example resin composition, and (FIG. 5D) an example of a cured and patterned first example resin composition.

An example of the first resin composition disclosed herein was prepared with epoxycyclohexyl POSS (about 13 wt %) and glycidyl POSS (about 4 wt %), diphenyl(2,4,6-trimethylbenzoyl)phosphine oxide (about 0.34 wt %) as the photoinitiator, TEGO® PC 1467 (about 0.85 wt %) as the photoacid generator, and about 1.4 wt % polyacrylate (BYK®-350). The components were mixed in a solvent (PGMEA) which made up the balance of the composition. The example of the first resin was deposited by spin coating (at 2200 rpm for about 1 minute) on a 3 inch silicon wafer. After deposition, the first resin composition was exposed to a softbake for about 2 minutes at about 120° C. to drive off PGMEA. The deposited resin composition was then imprinted using nanoimprint lithography. A working stamp was pressed into the deposited composition and the resin was exposed to UV curing with an LED UV lamp for about 20 seconds. Hard baking at 250° C. for about 10 minutes was also performed after the working stamp was removed. A black and white reproduction of the original colored image of the cured, patterned resin is shown in FIG. 5A.

Figure 5B:
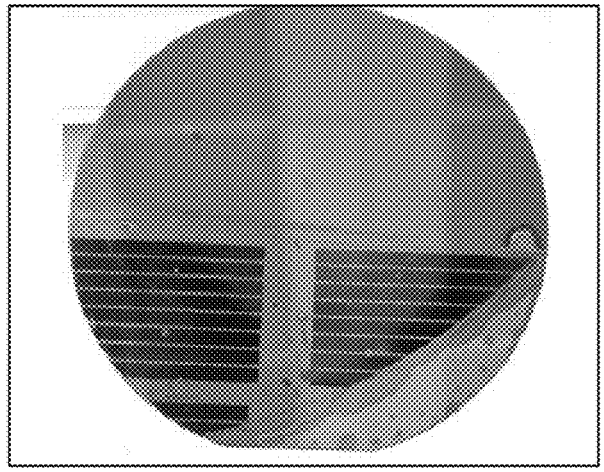

An example of second resin composition disclosed herein was prepared. This resin included epoxycyclohexyl POSS (about 13 wt %) and glycidyl POSS (about 4 wt %) as the epoxy resin matrix, diaryliodonium hexafluoroantimonate (SYLANTO™ 7MS from Synthos Specialties) (about 0.85 wt %) as the direct photoacid generator, and about 1.4 wt % polyacrylate (BYK®-350). The components were mixed in a solvent (PGMEA) which made up the balance of the composition. The example of the second resin was deposited by spin coating (at 2200 rpm for about 1 minute) on a 3 inch silicon wafer. After deposition, the second resin composition was exposed to a softbake for about 2 minutes at about 120° C. to drive off PGMEA. The deposited resin composition was then imprinted using nanoimprint lithography. A working stamp was pressed into the deposited composition and the resin was exposed to UV curing with an LED UV lamp for about 20 seconds. Hard baking at 250° C. for about 10 minutes was also performed after the working stamp was removed. A black and white reproduction of the original colored image of the cured, patterned resin is shown in FIG. 5B.

Figure 5C:
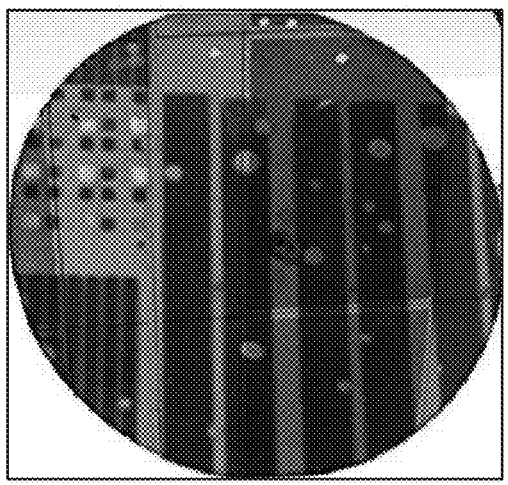

Another example of the first resin composition disclosed herein was prepared with epoxycyclohexyl POSS (about 13 wt %) and glycidyl POSS (about 4 wt %), ethyl(2,4,6-trimethylbenzoyl)phenylphosphinate (about 0.34 wt %) as the photoinitiator, TEGO® PC 1467 (about 0.85 wt %) as the photoacid generator, and about 1.4 wt % polyacrylate (BYK®-350). The components were mixed in a solvent (PGMEA) which made up the balance of the composition. This example of the first resin was deposited by spin coating (at 2200 rpm for about 1 minute) on a 3 inch silicon wafer. After deposition, the first resin composition was exposed to a softbake for about 2 minutes at about 120° C. to drive off PGMEA. The deposited resin composition was then imprinted using nanoimprint lithography. A working stamp was pressed into the deposited composition and the resin was exposed to UV curing with an LED UV lamp for about 20 seconds. Hard baking at 250° C. for about 10 minutes was also performed after the working stamp was removed. A black and white reproduction of the original colored image of the cured, patterned resin is shown in FIG. 5C.

Figure 5D:
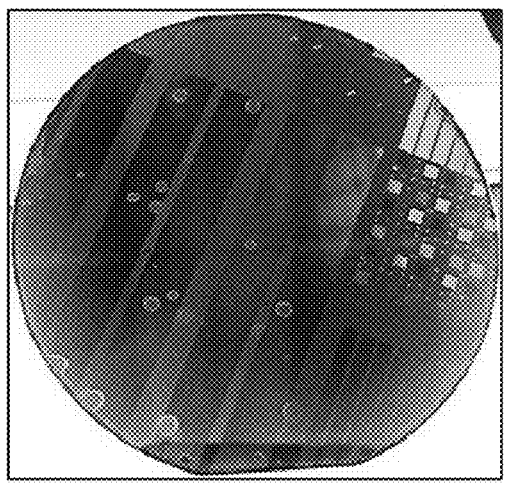

Still another example of the first resin composition disclosed herein was prepared with epoxycyclohexyl POSS (about 13 wt %) and glycidyl POSS (about 4 wt %), 2,2-dimethoxy-2-phenylacetophenone (about 0.34 wt %) as the photoinitiator, TEGO® PC 1467 (about 0.85 wt %) as the photoacid generator, and about 1.4 wt % polyacrylate (BYK®-350). The components were mixed in a solvent (PGMEA) which made up the balance of the composition. This example of the first resin was deposited by spin coating (at 2200 rpm for about 1 minute) on a 3 inch silicon wafer. After deposition, the first resin composition was exposed to a softbake for about 2 minutes at about 120° C. to drive off PGMEA. The deposited resin composition was then imprinted using nanoimprint lithography. A working stamp was pressed into the deposited composition and the resin was exposed to UV curing with an LED UV lamp for about 20 seconds. Hard baking at 250° C. for about 10 minutes was also performed after the working stamp was removed. A black and white reproduction of the original colored image of the cured, patterned resin is shown in FIG. 5D.

These images demonstrate that different examples of the first and second resin compositions disclosed herein can be nanoimprinted to form suitable depressions for flow cells or other suitable applications. It is believed that these cured and patterned resins will also exhibit low autofluorescence when exposed to blue and/or green excitation wavelengths.

Example 3

Nine resin compositions were prepared. Three of the compositions were comparative examples (including a comparative photoinitiator/photoacid generator combination), one of the compositions was a quencher example (including a quencher with a comparative photoinitiator/photoacid generator combination), and five of the compositions were example photoinitiator/photoacid generator combinations. Table 1 depicts the various components of the various resins. The components were mixed together with the same amount (about 1.4 wt %) of BYK 350 polyacrylate. Each sample was diluted with PGMEA so that the final composition included from about 17 wt % to about 22 wt % of resin composition components (epoxy resin, photoinitiator and/or photoacid generator, quencher (if included), and polyacrylate), with the balance being PGMEA.

TABLE 1

| Sample ID | Epoxy Resins | Photoinitiator | Photoacid Generator | Quencher |
|---|---|---|---|---|
| Comp. 1 | epoxycyclohexyl POSS (~10 wt %) and glycidyl POSS (~7 wt %) | thioxanth-9-one (ITX) (~0.34 wt %) | TEGO ® PC 1467 (~0.85 wt %) | None |

TABLE 1-continued

| Sample ID | Epoxy Resins | Photoinitiator | Photoacid Generator | Quencher |
|---|---|---|---|---|
| Comp. 2 | epoxycyclohexyl POSS (~10 wt %) and glycidyl POSS (~7 wt %) | thioxanth-9-one (ITX) (~0.34 wt %) | TEGO ® PC 1467 (~0.85 wt %) | None |
| Comp. 3 | epoxycyclohexyl POSS (~10 wt %) and glycidyl POSS (~7 wt %) | thioxanth-9-one (ITX) (~0.34 wt %) | Ferrocene (~0.85 wt %) | None |
| Ex. 1 | epoxycyclohexyl POSS (~10 wt %) and glycidyl POSS (~7 wt %) | None | diaryliodonium hexafluorophosphonate (SYLANTO ™ 7MP) (direct PAG) (~0.85 wt %) | None |
| Ex. 2 | epoxycyclohexyl POSS (~10 wt %) and glycidyl POSS (~7 wt %) | None | diaryliodonium hexafluoroantimonate (SYLANTO ™ 7MS) (direct PAG) (~0.85 wt %) | None |
| Ex. 3 | epoxycyclohexyl POSS (~10 wt %) and glycidyl POSS (~7 wt %) | 2,2-dimethoxy-2-phenylacetophenone (~0.34 wt %) | TEGO ® PC 1467 (~0.85 wt %) | None |
| Ex. 4 | epoxycyclohexyl POSS (~10 wt %) and glycidyl POSS (~7 wt %) | Phenylbis(2,4,6-trimethylbenzoyl)phosphine oxide (~0.34 wt %) | TEGO ® PC 1467 (~0.85 wt %) | None |
| Ex. 5 | epoxycyclohexyl POSS (~10 wt %) and glycidyl POSS (~7 wt %) | Diphenyl(2,4,6-trimethylbenzoyl)phosphine oxide (~0.34 wt %) | TEGO ® PC 1467 (~0.85 wt %) | None |
| Quencher 1 | epoxycyclohexyl POSS (~10 wt %) and glycidyl POSS (~7 wt %) | thioxanth-9-one (ITX) (~0.34 wt %) | TEGO ® PC 1467 (~0.85 wt %) | Dabcyl (~0.85 wt %) |

Each sample was deposited via spin coating (at 2200 rpm for about 1 minute) onto a silicon wafer. After deposition, the respective compositions were exposed to a softbake for about 2 minutes at about 120° C. to drive off PGMEA. The respective resin compositions were then exposed to UV curing with an LED UV lamp for about 20 seconds. Hard baking at 250° C. for about 10 minutes was also performed.

Figure 6:
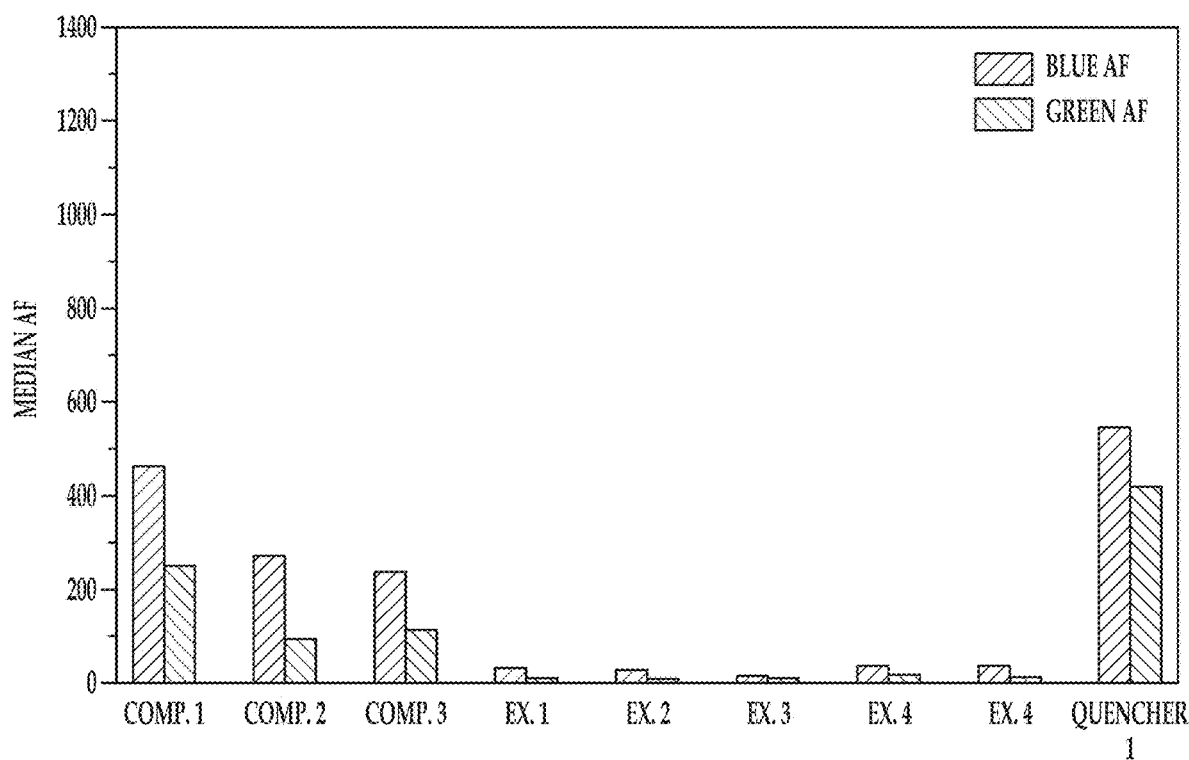
FIG. 6 is a graph depicting simulated autofluorescence results (in terms of median AF) for comparative and example resin compositions.

Each of the cured samples (comparative examples, examples, and quencher example) was respectively exposed to blue excitation wavelengths and green excitation wavelengths and the resulting autofluorescence was measured via high resolution imaging. FIG. 6 depicts the median autofluorescence results for each of the comparative resins, the quencher resin, and the example resins. As shown, example resins Ex. 1-5 had much lower autofluorescence than the comparative photoinitiator/photoacid generator combinations used in Comp. 1, Comp. 2, Comp. 3 and Quencher 1.

Each of the samples in Example 3 was also tested using another autofluorescence tool. While the results are not shown, there was a strong correlation between the results shown in FIG. 6 and the results from this other tool.

Each sample was also deposited via spin coating (at 2200 rpm for about 1 minute) onto a silicon wafer and was nanoimprinted. After deposition, the respective compositions were exposed to a softbake for about 2 minutes at about 120° C. to drive off PGMEA, and then a working stamp was pressed into the resin composition. The respective resin compositions were then exposed to UV curing with an LED UV lamp for about 20 seconds. Hard baking at 250° C. for about 10 minutes was also performed after removal of the working stamp. Each of the comparative examples, examples, and quencher example was successfully nanoimprinted.

Example 4

Sample Ex. 5, made with diphenyl(2,4,6-trimethylbenzoyl)phosphine oxide (TPO) as the photoinitiator, showed very low autofluorescence in Example 3. As such, variations of this example resin were prepared with different amounts of the photoinitiator. The amounts of the epoxy and the photoacid generator remained the same. Example resin compositions 5A, 5B, 5C, and 5D were prepared, respectively, with 0.25 times the amount of TPO as in Example 3, 0.5 times the amount of TPO as in Example 3, the same amount of TPO as in Example 3 (i.e., 1 times the amount), and 2 times the amount of TPO as in Example 3. The Comp. 1 and Comp. 2 resin formulations from Example 3 were also used in this example.

Each sample was deposited via spin coating (at 2200 rpm for about 1 minute) onto glass substrates. After deposition, the respective compositions were exposed to a softbake for about 2 minutes at about 120° C. to drive off PGMEA. The respective resin compositions were then exposed to UV curing with an LED UV lamp for about 20 seconds. Hard baking at 250° C. for about 10 minutes was also performed.

Figure 7:
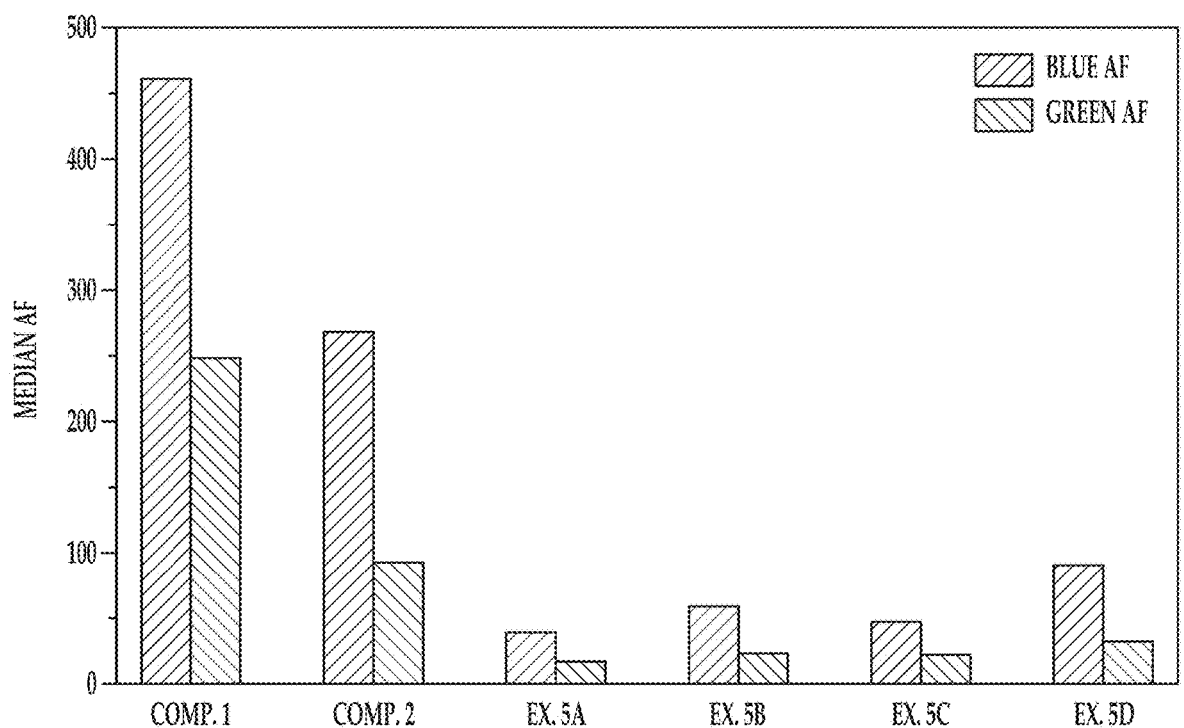
FIG. 7 is a graph depicting simulated autofluorescence results (in terms of median AF) for comparative and example resin compositions.

Each of the cured samples (comparative examples and examples 5A-5D) was respectively exposed to blue excitation wavelengths and green excitation wavelengths and the resulting autofluorescence was measured via high resolution imaging. FIG. 7 depicts the median autofluorescence results for each of the comparative resins, and the example resins formulated with different amount of TPO. As shown, example resins Ex. 5A through 5D had much lower autofluorescence than the comparative photoinitiator/photoacid generator combinations used in Comp. 1, Comp. 2. The autofluorescence went up with increasing amounts of TPO, but the levels were still less than the comparative examples.

The example resin compositions 5A-5D were also respectively deposited via spin coating (at 2200 rpm for about 1 minute) onto glass and silicon substrates and were nanoimprinted. After deposition, the respective compositions were exposed to a softbake for about 2 minutes at about 120° C. to drive off PGMEA, and then a working stamp was pressed into the resin composition. The respective resin compositions were then exposed to UV curing with an LED UV lamp for about 20 seconds. Hard baking at 250° C. for about 10 minutes was also performed. Each of the examples resin compositions 5A-5D was successfully nanoimprinted on each of the substrate types.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range from about 380 nm to about 480 nm, should be interpreted to include not only the explicitly recited limits of from about 380 nm to about 480 nm, but also to include individual values, such as about 408 nm, about 445.5 nm, etc., and sub-ranges, such as from about 425 nm to about 475 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A resin composition, consisting of:
   an epoxy resin matrix comprising an epoxy material selected from the group consisting of tetrakis(epoxycyclohexyl ethyl)tetramethyl cyclotetrasiloxane; a copolymer of (epoxycyclohexylethyl)methylsiloxane and dimethylsiloxane; 1,3-bis[2-(3,4-epoxycyclohexyl) ethyl] tetramethyl disiloxane; 1,3-bis(glycidoxypropyl)tetramethyl disiloxane; and combinations thereof;
   a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide;
   a photoacid generator;
   a polyacrylate; and
   a solvent selected from the group consisting of propylene glycol monomethyl ether acetate (PGMEA), toluene, dimethyl sulfoxide (DMSO), and tetrahydrofuran (THF).

2. The resin composition as defined in claim 1, wherein the free radical photoinitiator is the phosphine oxide, and wherein the phosphine oxide is selected from the group consisting of diphenyl(2,4,6-trimethylbenzoyl)phosphine oxide; a blend of diphenyl(2,4,6-trimethylbenzoyl)phosphine oxide and 2-hydroxy-2-methylpropiophenone; phenylbis(2,4,6-,trimethylbenzoyl)phosphine oxide; ethyl(2,4,6-trimethylbenzoyl)phenylphosphinate; and combinations thereof.

3. The resin composition as defined in claim 1, wherein the photoacid generator is selected from the group consisting of N-hydroxynaphthalimide triflate; triarylsulfonium hexafluorophosphate salts, mixed; triarylsulfonium hexafluoroantimonate salts, mixed; 1-naphthyl diphenylsulfonium triflate; 4-phenylthiophenyl)diphenylsulfonium triflate; bis-(4-methylphenyl)iodonium hexafluorophosphate; bis(4-tert-butylphenyl)iodonium hexafluorophosphate; (2-methylphenyl)(2,4,6-trimethylphenyl)iodonium triflate; bis(2,4,6-trimethylphenyl)iodonium triflate; bis-(4-dedecylphenyl)iodonium hexafluoroantimonate salt; and combinations thereof.

4. The resin composition as defined in claim 1, wherein the free radical photoinitiator and the photoacid generator together are present in an amount ranging from about 1 wt % to about 10 wt %.

5. The resin composition as defined in claim 1, wherein the solvent is the propylene glycol monomethylether acetate (PGMEA).

6. A method of making a flow cell, comprising:
   depositing a resin composition on a substrate, the resin composition consisting of:
      an epoxy resin matrix comprising an epoxy material selected from the group consisting of tetrakis(epoxycyclohexyl ethyl)tetramethyl cyclotetrasiloxane; a copolymer of (epoxycyclohexylethyl)methylsiloxane and dimethylsiloxane; 1,3-bis[2-(3,4-epoxycyclohexyl) ethyl] tetramethyl disiloxane; 1,3-bis(glycidoxypropyl)tetramethyl disiloxane; and combinations thereof;
      a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide;
      a photoacid generator;
      a polyacrylate; and
      a solvent selected from the group consisting of propylene glycol monomethyl ether acetate (PGMEA), toluene, dimethyl sulfoxide (DMSO), and tetrahydrofuran (THF);
   nanoimprinting the deposited resin composition using a working stamp; and
   curing the deposited resin composition to form a cured, patterned resin.

7. A resin composition, comprising:
   an epoxy resin matrix;
   a free radical photoinitiator selected from the group consisting of 2-ethyl-9,10-dimethoxyanthracene, 2,2-dimethoxy-2-phenylacetophenone, 2-ethoxy-2-phenylacetophenone, and a phosphine oxide;

a photoacid generator;

a solvent selected from the group consisting of propylene glycol monomethyl ether acetate (PGMEA), toluene, dimethyl sulfoxide (DMSO), and tetrahydrofuran (THF); and a dark quencher selected from the group consisting of an azo dye, 4-dimethylaminobenzene-4'-carboxylic acid, dabcyl azide, dabsyl azide, disperse red 19, a black dye-based quencher, and combinations thereof.

8. The resin composition as defined in claim 7, wherein the dark quencher is the 4-dimethylaminobenzene-4'-carboxylic acid, dabcyl azide, dabsyl azide, disperse red 19, a black dye-based quencher, or a combination thereof.

9. The resin composition as defined in claim 7, wherein the solvent is the propylene glycol monomethyl ether acetate (PGMEA).

* * * * *

UNITED STATES PATENT AND TRADEMARK OFFICE
CERTIFICATE OF CORRECTION

| | | |
|---|---|---|
| PATENT NO. | : 12,013,330 B2 | Page 1 of 1 |
| APPLICATION NO. | : 16/515849 | |
| DATED | : June 18, 2024 | |
| INVENTOR(S) | : Timothy J. Merkel et al. | |

It is certified that error appears in the above-identified patent and that said Letters Patent is hereby corrected as shown below:

In the Claims

Column 48, Line 15:
In Claim 2, delete "(2,4,6-,trimethylbenzoyl)" and insert -- (2,4,6-trimethylbenzoyl) --.

Column 48, Line 28:
In Claim 3, delete "bis-(4-dedecylphenyl)iodonium" and insert -- bis-(4-dodecylphenyl)iodonium --.

Signed and Sealed this
Twenty-second Day of October, 2024

Katherine Kelly Vidal
*Director of the United States Patent and Trademark Office*